United States Patent
Lee et al.

(10) Patent No.: US 11,529,188 B2
(45) Date of Patent: Dec. 20, 2022

(54) SURGICAL INSTRUMENT FOR ELECTROCAUTERY

(71) Applicant: LivsMed Inc., Seongnam-si (KR)

(72) Inventors: Jung Joo Lee, Seongnam-si (KR); Heejin Kim, Seongnam-si (KR); Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 17/511,890

(22) Filed: Oct. 27, 2021

(65) Prior Publication Data

US 2022/0125503 A1 Apr. 28, 2022

(30) Foreign Application Priority Data

Oct. 27, 2020 (KR) .......................... 10-2020-0140113

(51) Int. Cl.
  *A61B 18/14* (2006.01)
  *A61B 18/00* (2006.01)
  *A61B 18/12* (2006.01)

(52) U.S. Cl.
  CPC ...... *A61B 18/1482* (2013.01); *A61B 18/1442* (2013.01); *A61B 2018/00083* (2013.01); *A61B 2018/00202* (2013.01); *A61B 2018/00595* (2013.01); *A61B 2018/1253* (2013.01)

(58) Field of Classification Search
  CPC . A61B 18/14; A61B 18/1442; A61B 18/1482; A61B 2018/00083; A61B 2018/00202; A61B 2018/00595; A61B 2018/1253
  USPC .............................. 606/51–52, 169, 205–207
  See application file for complete search history.

(56) References Cited

U.S. PATENT DOCUMENTS

| | | | |
|---|---|---|---|
| 6,394,998 | B1 | 5/2002 | Wallace et al. |
| 6,840,938 | B1 * | 1/2005 | Morley .................. A61B 34/71 901/29 |
| 2007/0208375 | A1 | 9/2007 | Nishizawa et al. |
| 2009/0082768 | A1 | 3/2009 | Bacher et al. |
| 2015/0150635 | A1 | 6/2015 | Kilroy et al. |

FOREIGN PATENT DOCUMENTS

| | | |
|---|---|---|
| JP | 59-102587 A | 6/1984 |
| JP | 2000-70280 A | 3/2000 |
| JP | 2010-220786 A | 10/2010 |
| KR | 10-1064825 B1 | 9/2011 |
| KR | 10-2012-0003091 A | 1/2012 |
| WO | 2019/069181 A1 | 4/2019 |

\* cited by examiner

*Primary Examiner* — Khadijeh A Vahdat
(74) *Attorney, Agent, or Firm* — Bridgeway IP Law Group, PLLC; Sang Ho Lee; Hyun Woo Shin

(57) ABSTRACT

A surgical instrument for electrocautery is provided. The surgical instrument is a manually operable surgical instrument for electrocautery for use in laparoscopic surgery or various surgeries.

11 Claims, 25 Drawing Sheets

SURGICAL INSTRUMENT FOR ELECTROCAUTERY

CROSS-REFERENCE TO RELATED APPLICATION

This application is based on and claims priority under 35 U.S.C. § 119 to Korean Patent Application No. 10-2020-0140113, filed on Oct. 27, 2020, in the Korean Intellectual Property Office, the disclosure of which is incorporated by reference herein in its entirety.

BACKGROUND

1. Field

One or more embodiments relates to a surgical instrument for electrocautery, and more particularly, to a surgical instrument for electrocautery with enhanced insulating ability between jaws and wires in a manually operable surgical instrument for use in laparoscopic surgery or various surgeries.

2. Description of the Related Art

Surgical operations in many cases require cutting and joining of body tissues including organs, muscular tissues, connective tissues, and blood vessels. Over the centuries, sharp blades and sutures have been used for cutting and joining. However, bleeding occurs when cutting body tissues, in particular, relatively highly vascularized tissue during surgical operation. Therefore, doctors have been in need of surgical instruments and methods to slow or reduce bleeding during surgical operations.

Recently, it has become possible to use an electric surgical instrument that uses electrical energy to perform certain surgical tasks. For example, in surgical instruments such as graspers, scissors, tweezers, blades, needles, and hooks, electric surgical instruments including one or more electrodes formed to supply electric energy have been developed. Electrical energy supplied through the electrodes may be used to coagulate, bond, or cut the patient's body tissues. In particular, when electrical energy is used, amputation and hemostasis may be performed at the same time.

Electric surgical instruments are typically divided into two types: monopolar and bipolar. In a monopolar electric surgical instrument, electrical energy of a specific polarity is supplied to one or more electrodes of the instrument. And electricity of different polarity is electrically connected to the patient. In a bipolar electric surgical instrument, one or more electrodes are electrically connected to a first polarity electrical energy source, and one or more electrodes are electrically connected to a second polarity electrical energy source opposite to the first polarity.

The above-mentioned background art is technical information possessed by the inventor for the derivation of the present disclosure or acquired during the derivation of the present disclosure, and cannot necessarily be said to be a known technique disclosed to the general public prior to the filing of the present disclosure.

SUMMARY

One or more embodiments include a surgical instrument for electrocautery with enhanced insulating ability between jaws and wires, in a manually operable surgical instrument for use in laparoscopic surgery or various surgeries.

Additional aspects will be set forth in part in the description which follows and, in part, will be apparent from the description, or may be learned by practice of the presented embodiments of the disclosure.

According to one or more embodiments, a surgical instrument for electrocautery includes an end tool including at least one jaw formed to be rotatable and an end tool pulley in which a shaft through portion, into which a rotation shaft of the jaw is inserted therethrough, is formed and in which at least a portion of the jaw is accommodated; a manipulation portion for controlling rotation of the end tool in two or more directions; a power transmission portion including a wire connected to the manipulation portion and transferring the rotation of the manipulation portion to the jaw; and a connection portion extending in a first direction (X-axis), having one end coupled to the end tool and the other end coupled to the manipulation portion, and connecting the manipulation portion and the end tool, wherein the end tool pulley is formed of an insulator.

In an embodiment of the present disclosure, the end tool further includes an electric wire connected to the jaw and passing through an inside of the end tool pulley; and an end tool hub axially coupled so that the end tool pulley coupled the jaw is rotatable, and the jaws may be formed to be spaced apart from the shaft through portion to a certain extent.

In an embodiment of the present disclosure, the jaw includes a pinching portion, an extended portion extending in one direction from the pinching portion, and a locking portion protruding from the extended portion, the end tool pulley includes a coupling portion formed in a portion connected to the jaw and a jaw receiving portion formed in a shape corresponding to the extended portion inside the coupling portion, and at least a portion of the extended portion may be received and coupled to the jaw receiving portion.

In an embodiment of the present disclosure, the locking portion is formed to be caught on the jaw receiving portion of the end tool pulley, and the jaw may be prevented from being detached from the end tool pulley.

In an embodiment of the present disclosure, the coupling portion may be formed to protrude to a certain extent from a main body of an upper plate of the end tool pulley toward the jaw.

In an embodiment of the present disclosure, a creepage distance between the wire and the jaw may be increased by the coupling portion.

In an embodiment of the present disclosure, the wire and the jaw may be electrically insulated by the end tool pulley.

In an embodiment of the present disclosure, the end tool pulley may include ceramic.

In an embodiment of the present disclosure, the surgical instrument for electrocautery may be monopolar type.

In an embodiment of the present disclosure, the shaft through portion of the end tool pulley and the jaw may be not in contact.

Other aspects, features and advantages other than those described above will become apparent from the following detailed description of the drawings, claims and disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1A:
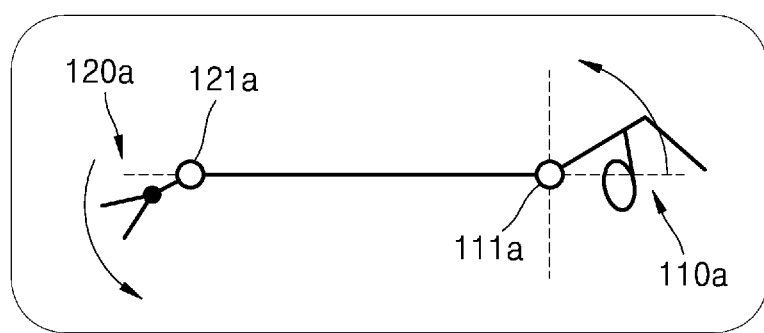
FIG. 1A is a conceptual diagram of pitch motion of a conventional surgical instrument.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The present disclosure may include various embodiments and modifications, and particular embodiments thereof are illustrated in the drawings and will be described herein in detail. However, it will be understood that the present disclosure is not limited to the embodiments and includes all modifications, equivalents, and replacements within the idea and technical scope of the present disclosure. Moreover, detailed descriptions related to well-known functions or configurations will be omitted in order not to unnecessarily obscure subject matters of the present disclosure.

Although terms such as "first" and "second" may be used herein to describe various elements or components, these elements or components should not be limited by these terms. These terms are only used to distinguish one element or component from other elements or components.

The terminology used herein is for explaining specific embodiments only and is not intended to limit the present disclosure. As used herein, the singular forms "a," "an", and "the" are intended to include the plural forms as well, unless the context clearly indicates otherwise. It will be understood that terms such as "comprise," "include," and "have," when used herein, specify the presence of state features, integers, steps, operations, elements, components, or combinations thereof, but do not preclude the presence or addition of one or more other features, integers, steps, operations, elements, components, or combinations thereof.

Hereinafter, embodiments of the present disclosure will be described in detail with reference to the accompanying drawings. In the following description, like reference numerals denote like elements, and redundant descriptions thereof will be omitted.

In addition, it will be understood that various embodiments of the present disclosure may be interpreted or implemented in combination, and technical features of each embodiment may be interpreted or implemented in combination with technical features of other embodiments.

An instrument for surgery of the present disclosure is characterized in that if a manipulation part is rotated in one direction for at least any one of pitch, yaw, and actuation motions, an end tool is rotated in intuitively the same direction as the direction in which the manipulation part is manipulated.

Figure 1B:
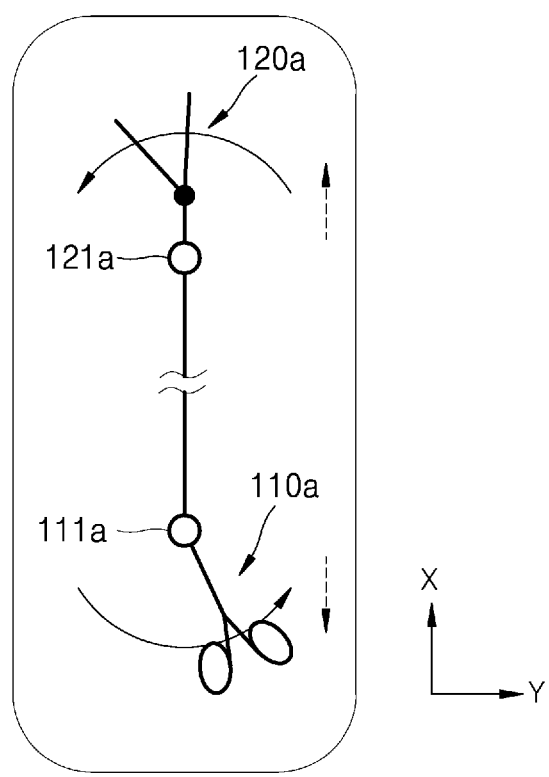
FIG. 1B is a conceptual diagram of yaw motion.

FIG. 1A is a schematic view illustrating pitch motion of an instrument for surgery of the related art, and FIG. 1B is a schematic view illustrating yaw motion of the instrument for surgery of the related art.

Referring to FIG. 1A, a pitch motion of the instrument for surgery of the related art is performed as follows. In a state in which an end tool 120a is in front of an end tool rotation center 121a and a manipulation part 110a is in back of a manipulation part rotation center 111a, if the manipulation part 110a is rotated clockwise, the end tool 120a is also rotated clockwise, and if the manipulation part 110a is rotated counterclockwise, the end tool 120a is also rotated counterclockwise. Referring to FIG. 1B, a yaw motion of the instrument for surgery of the related art is performed as follows. In a state in which the end tool 120a is in front of the end tool rotation center 121a and the manipulation part 110a is in back of the manipulation part rotation center 111a, if the manipulation part 110a is rotated clockwise, the end tool 120a is also rotated clockwise, and if the manipulation part 110a is rotated counterclockwise, the end tool 120a is also rotated counterclockwise. In this case, from the viewpoint of a horizontal direction of a user, when the user moves the manipulation part 110a to the left, the end tool 120a moves to the right, and when the user moves the manipulation part 110a to the right, the end tool 120a moves to the left. Consequently, since the manipulation direction of the user and the operation direction of the end tool are opposite each other, the user may make mistakes and have difficulty in manipulation.

Figure 1C:
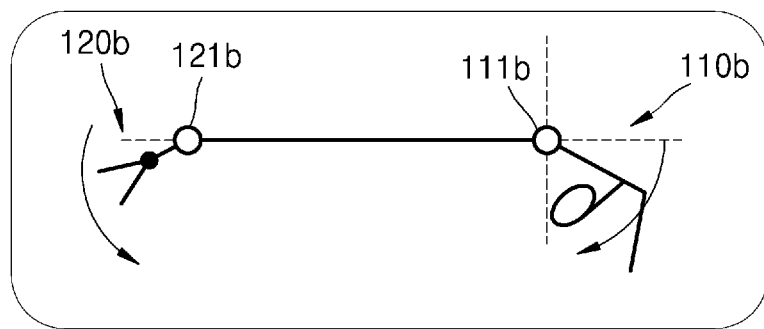
FIG. 1C is a conceptual diagram of pitch motion of another conventional surgical instrument.
Figure 1D:
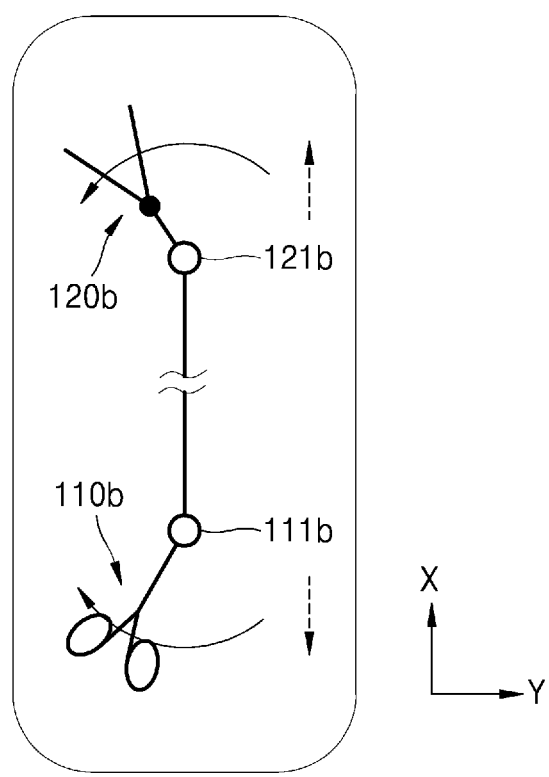
FIG. 1D is a conceptual diagram of yaw motion.

FIG. 1C is a schematic view illustrating a pitch motion of another instrument for surgery of the related art, and FIG. 1D is a schematic view illustrating a yaw motion of the instrument for surgery of the related art.

Figure 1E:
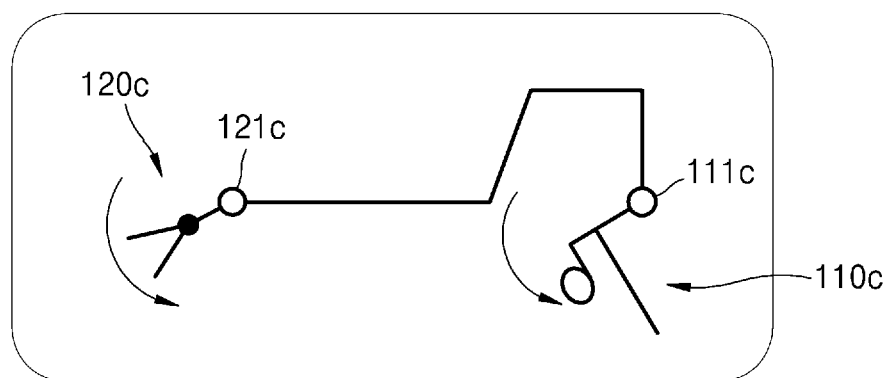
FIG. 1E is a conceptual diagram of pitch motion of a surgical instrument according to the present disclosure.
Figure 1F:
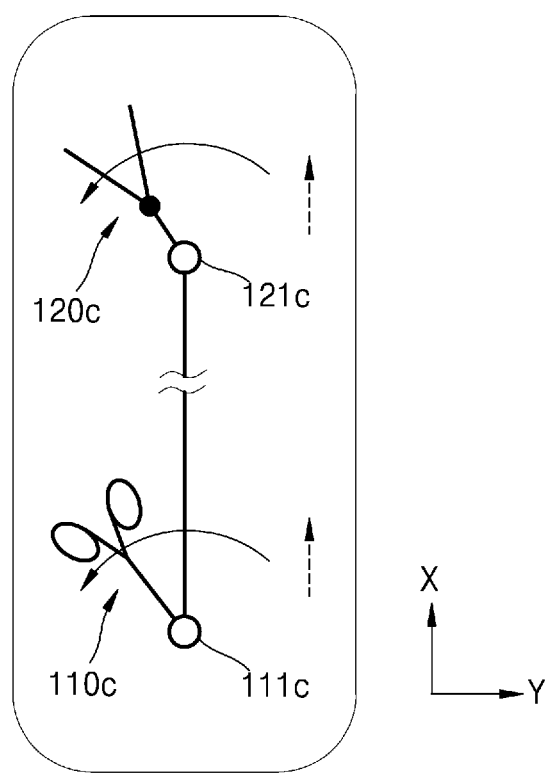
FIG. 1F is a conceptual diagram of yaw motion.

Referring to FIG. 1C, some instruments for surgery of the related art have a mirror-symmetric structure and perform a pitch motion as follows: in a state in which an end tool 120*b* is formed in front of an end tool rotation center 121*b* and an manipulation part 110*b* is formed in back of a manipulation part rotation center 111*b*, when the manipulation part 110*b* is rotated clockwise, the end tool 120*b* is rotated counter-clockwise, and when the manipulation part 110*b* is rotated counterclockwise, the end tool 120*b* is rotated clockwise. In this case, from the viewpoint of the rotation directions of the manipulation part 110*b* and the end tool 120*b*, the direction in which a user rotates the manipulation part 110*b* is opposite the direction in which the end tool 120*b* is accordingly rotated. Consequently, the user may confuse manipulation directions, and the operation of a joint may not be intuitive, thereby causing mistakes. In addition, referring to FIG. 1D, a yaw motion is performed as follows. In a state in which the end tool 120*b* is in front of the end tool rotation center 121*b* and the manipulation part 110*b* is in back of the manipulation part rotation center 111*b*, if the manipulation part 110*b* is rotated clockwise, the end tool 120*b* is rotated counterclockwise, and if the manipulation part 110*b* is rotated counterclockwise, the end tool 120*b* is rotated clockwise. In this case, from the viewpoint of the rotation directions of the manipulation part 110*b* and the end tool 120*b*, the direction in which a user rotates the manipulation part 110*b* is opposite the direction in which the end tool 120*b* is accordingly rotated. Consequently, the user may confuse manipulation directions, and the operation of the joint may not be intuitive, thereby causing mistakes. As described above, when a user performs a pitch or yaw motion of an instrument for surgery of the related art, the manipulation direction of the user is not the same as the operation direction of an end tool from the viewpoint of the rotation directions or the horizontal direction. This is because an end tool and a manipulation part of an instrument for surgery of the related art have different joint structures. That is, the end tool is formed in front of the rotation center of the end tool, whereas the manipulation part is formed in back of the rotation center of the manipulation part. In order to address this problem, instruments for surgery according to embodiments of the present disclosure illustrated in FIGS. 1E and 1F are characterized in that an end tool 120*c* is provided in front of an end tool rotation center 121*c* and a manipulation part 110*c* is also provided in front of a manipulation part rotation center 111*c*, such that the operations of the manipulation part 110*c* and the end tool 120*c* are intuitively identical to each other. In other words, unlike the configuration example of the related art in which the manipulation part is adjacent to a user (i.e., distant from the end tool) based on a joint thereof as illustrated in FIGS. 1A, 1B, 1C, and 1D, the instruments for surgery according to the embodiments of the present disclosure illustrated in FIGS. 1E and 1F are configured such that at least a portion of the manipulation part may be more adjacent to the end tool based on a joint thereof (i.e., than the joint thereof is to the end tool) at least a moment of manipulation.

In other words, in the case of an instrument for surgery of the related art as illustrated in FIGS. 1A, 1B, 1C, and 1D, since an end tool is located in front of a rotation center thereof but a manipulation part is located in back of a rotation center thereof, the end tool fixed at a rear side thereof and configured to be moved at a front side thereof is moved by the manipulation part fixed at a front side thereof and configured to be moved at a rear side thereof, and thus the structures of the manipulation part and the end tool are not intuitively identical to each other. Therefore, the manipulation of the manipulation part and the operation of the end tool are not identical to each other from the viewpoint of the horizontal direction or rotation directions, and thus a user may be confused and may not intuitively quickly manipulate the manipulation part, thereby making mistakes. However, in the case of the instruments for surgery according to the embodiments of the present disclosure, since each of the end tool and the manipulation part moves with respect to a rear rotation center thereof, it may be considered that the operations of the end tool and the manipulation part are structurally intuitively identical to each other. In other words, like the end tool having a portion movable based on the rear rotation center thereof, the manipulation part has a portion movable based on the rear rotation center thereof. Thus, it may be considered that the operations of the end tool and the manipulation part are structurally intuitively identical to each other. Consequently, a user may intuitively rapidly control the direction of the end tool, and the possibility that the user makes a mistake may be significantly reduced. A specific mechanism enabling this function will be described below.

Figure 2:
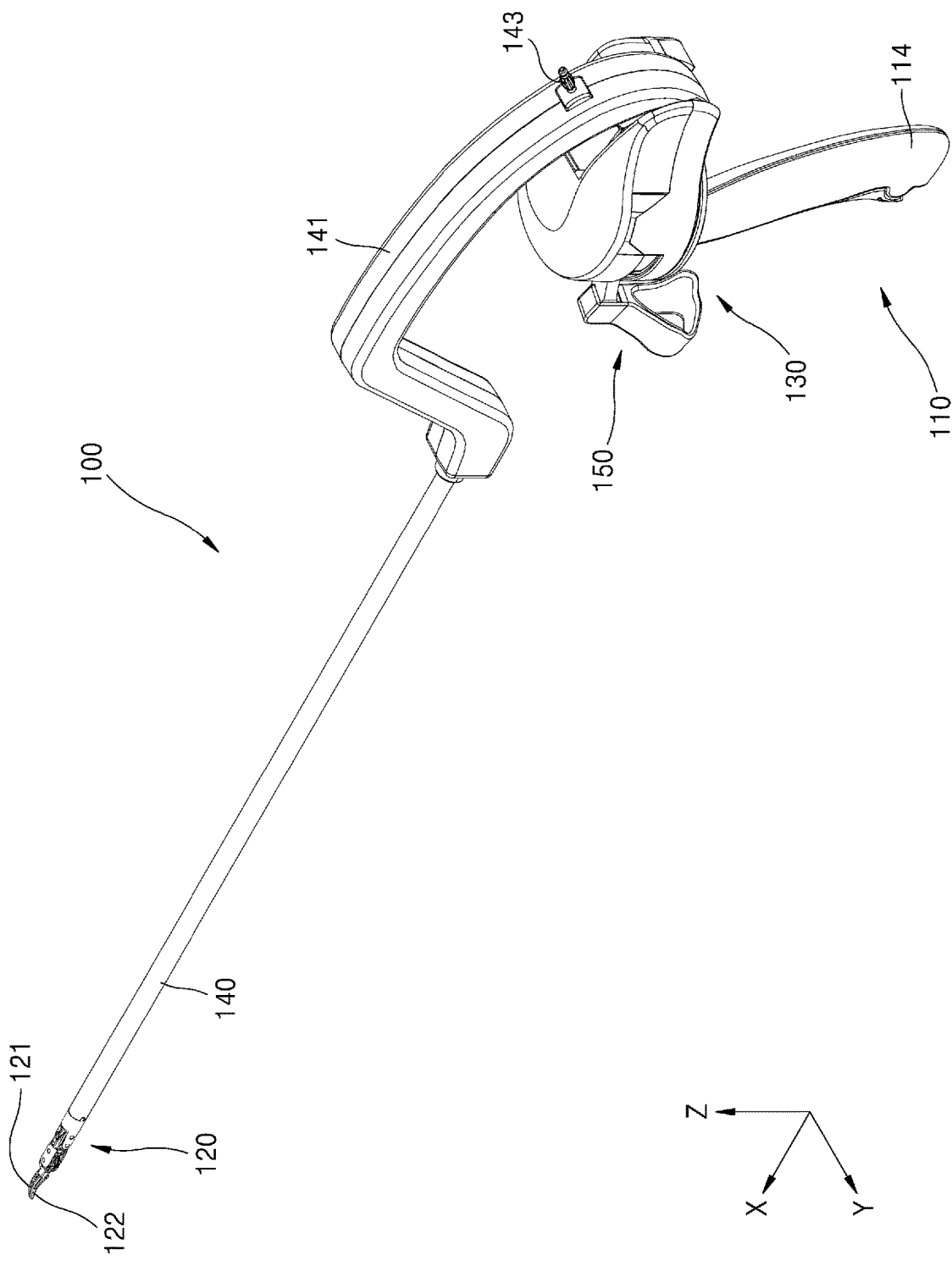
FIG. 2 is a perspective view illustrating a surgical instrument according to a first embodiment of the present disclosure.
Figure 3:
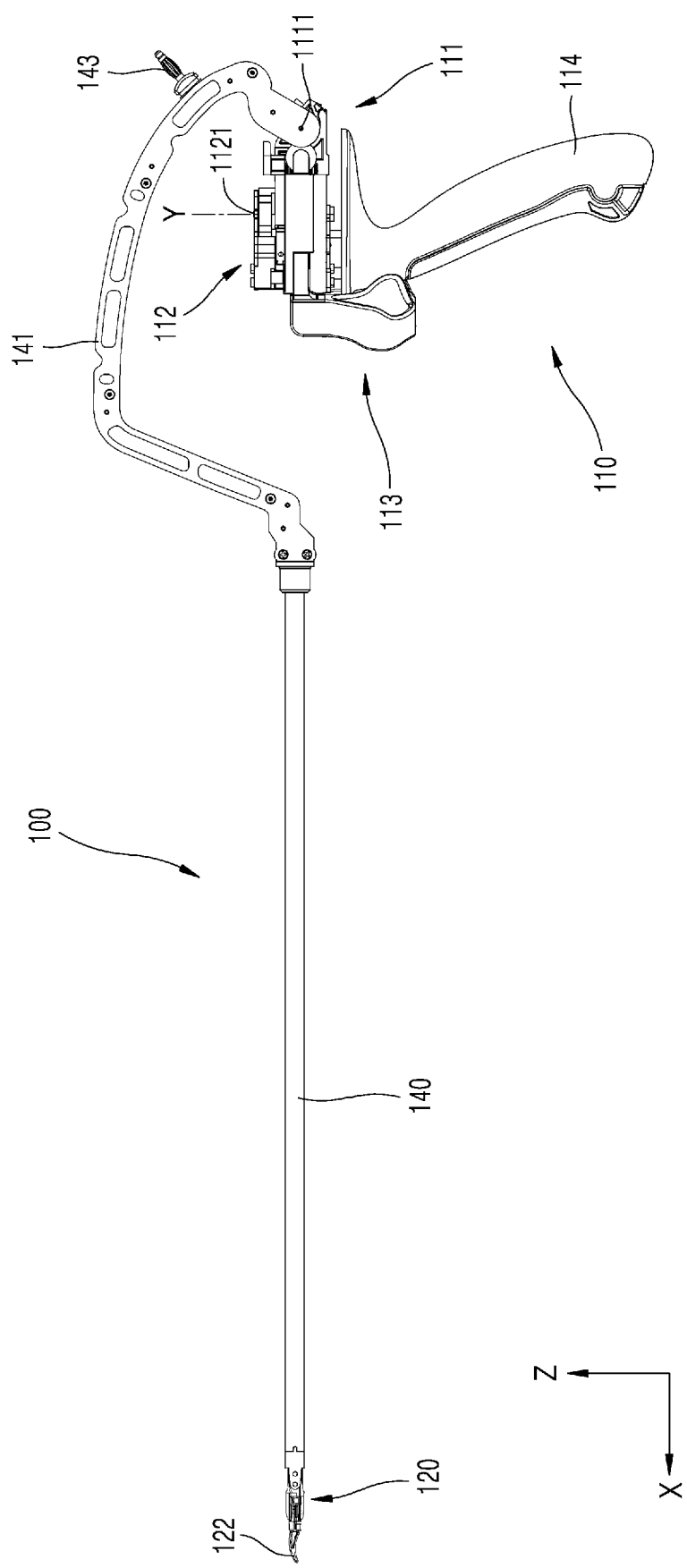
FIG. 3 is a side view of the surgical instrument of FIG. 2.

FIG. 2 is a perspective view illustrating an instrument for surgery according to a first embodiment of the present disclosure, and FIG. 3 is a side view illustrating the instrument for surgery shown in FIG. 2.

Referring to FIGS. 2, and 3, the instrument 100 for surgery according to the first embodiment of the present disclosure includes a manipulation part 110, an end tool 120, a power transmission part 130, a connecting part 140, and a ring handle 150. Here, the connecting part 140 may have a hollow shaft shape accommodating at least one wire (described later). The manipulation part 110 may be coupled to one end portion of the connecting part 140, and the end tool 120 may be coupled to the other end portion of the connecting part 140 such that the manipulation part 110 and the end tool 120 may be connected through the connecting part 140. Here, the connecting part 140 of the instrument 100 for surgery according to the first embodiment of the present disclosure is characterized by having a bent part 141 on a side of the manipulation part 110. As described above, an end portion of the connecting part 140 located on a side of the manipulation part 110 is bent such that a pitch manipulation part 111, a yaw manipulation part 112, and an actuation manipulation part 113 may be located on or adjacent to an extension line of the end tool 120. From another perspective, it may be stated that at least portions of the pitch manipulation part 111 and the yaw manipulation part 112 is accommodated in a concave region formed by the bent part 141. Owning to the shape of the bent part 141, the shapes and operations of the manipulation part 110 and the end tool 120 may be more intuitively identical to each other.

In addition, a plane formed by the bent part 141 may be substantially the same as a pitch plane, that is, an XZ plane shown in FIG. 2. In this manner, since the bent part 141 is provided on the same plane as the XZ plane, interference between manipulation parts may be reduced. Alternatively, any other configuration of the end tool and the manipulation part may be possible in addition to the XZ plane configuration.

Meanwhile, a connector 143 may be formed on the bent part 141. The connector 143 may be connected to an external power source (not shown), and the connector 143 may be connected to jaws 121 and 122 through an electric wire 168, and may deliver, to the jaws 121 and 122, the electric energy supplied from the external power source (not shown). Here, the connector 143 illustrated in the drawings is a monopolar-type electrode in which one electrode is formed. However, the inventive concept of the present disclosure is not limited thereto. In an embodiment, the connector 143 may be a bipolar type electrode.

The manipulation part 110 is provided on one end portion of the connecting part 140 and has an interface such as a tweezers shape, a stick shape, or a lever shape that a surgeon may directly manipulate, such that if an surgeon manipulates the interface, the end tool 120 connected to the interface and inserted into the body of a patient may be operated for surgery. Although FIG. 2 illustrates that the manipulation part 110 has a handle shape configured to be rotated by inserting a finger thereinto, the idea of the present disclosure is not limited thereto. That is, the manipulation part 110 may have any shape as long as the end tool 120 is connected to the manipulation part 110 and manipulated using the manipulation part 110.

The end tool 120 is provided on the other end portion of the connecting part 140 and is configured to be moved for surgery in a state in which that end tool 120 is inserted into a surgical site. As an example of the end tool 120, a pair of jaws 121 and 122 for gripping may be used as illustrated in FIG. 2. However, the idea of the present disclosure is not limited thereto. That is, various devices for surgery may be used as the end tool 120. For example, a device such as a one-armed cauter may be used as the end tool 120. The end tool 120 is connected to the manipulation part 110 through the power transmission part 130 to receive a driving force of the manipulation part 110 through the power transmission part 130, thereby performing a necessary surgical motion such as gripping, cutting, or suturing.

Herein, the end tool 120 of the instrument 100 for surgery of the first embodiment of the present disclosure is configured to rotate in at least two directions. For example, the end tool 120 may be capable of pitch motion around a Y axis of FIG. 2 and yaw motion and actuation motion around a Z axis of FIG. 2.

In the present disclosure, pitch, yaw, and actuation motions are defined as follows.

First, the pitch motion refers to upward and downward rotations of the end tool 120 with respect to an extension direction (the direction of an X axis in FIG. 2) of the connecting part 140, that is, rotation of the end tool 120 around the Y axis in FIG. 2. In other words, the pitch motion refers to upward and downward rotations of the end tool 120, which extends from the connecting part 140 in the extension direction (the X-axis direction in FIG. 2) of the connecting part 140, around the Y axis with respect to the connecting part 140. Next, the yaw motion refers to leftward and rightward rotations of the end tool 120 with respect to the extension direction (the X-axis direction in FIG. 2) of the connecting part 140, that is, rotation of the end tool 120 around the Z axis in FIG. 2. In other words, the yaw motion refers to leftward and rightward rotations of the end tool 120, which extends from the connecting part 140 in the extension direction (the X-axis direction in FIG. 2) of the connecting part 140, around the Z axis with respect to the connecting part 140. That is, the yaw motion refers to a motion in which the two jaws 121 and 122 of the end tool 120 are rotated around the Z axis in the same direction. In addition, the actuation motion refers to a motion in which the end tool 120 rotates around the same rotation axis as the yaw motion but the two jaws 121 and 122 rotate in opposite directions to move close to each other or away from each other. That is, the actuation motion refers to a motion in which the two jaws 121 and 122 rotate around the Z axis in opposite directions.

The power transmission part 130 may connect the manipulation part 110 and the end tool 120 to each other and transmit a driving force of the manipulation part 110 to the end tool 120. The power transmission part 130 may include a plurality of wires, pulleys, links, nodes, and gears. According to the embodiment of the present disclosure, the power transmission part 130 of the instrument 100 for surgery may include a pitch wire 130P, a first jaw wire 130J1, and a second jaw wire 130J2.

Hereinafter, parts of the instrument 100 for surgery shown in FIG. 2 such as the manipulation part 110, the end tool 120, and the power transmission part 130 will be described in more detail.

Figure 4:
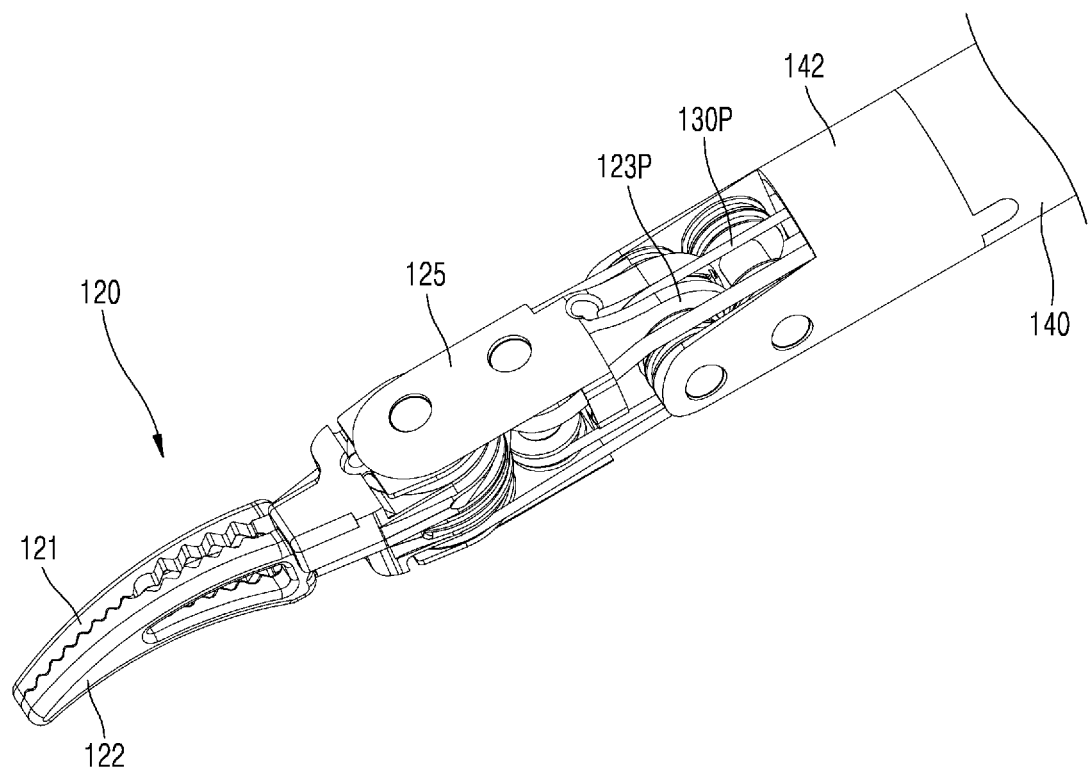
FIGS. 4 and 5 are perspective views illustrating an end tool of the surgical instrument of FIG. 2.
Figure 5:
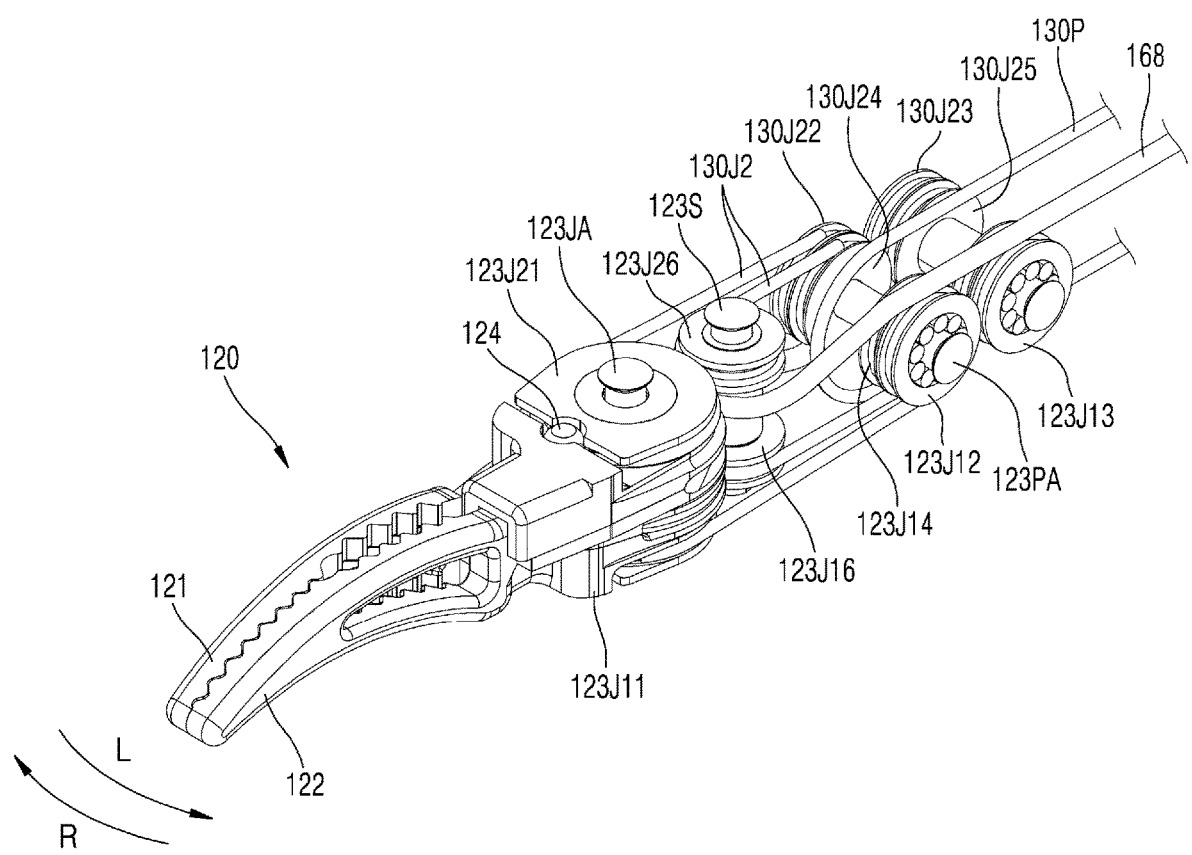
Figure 6:
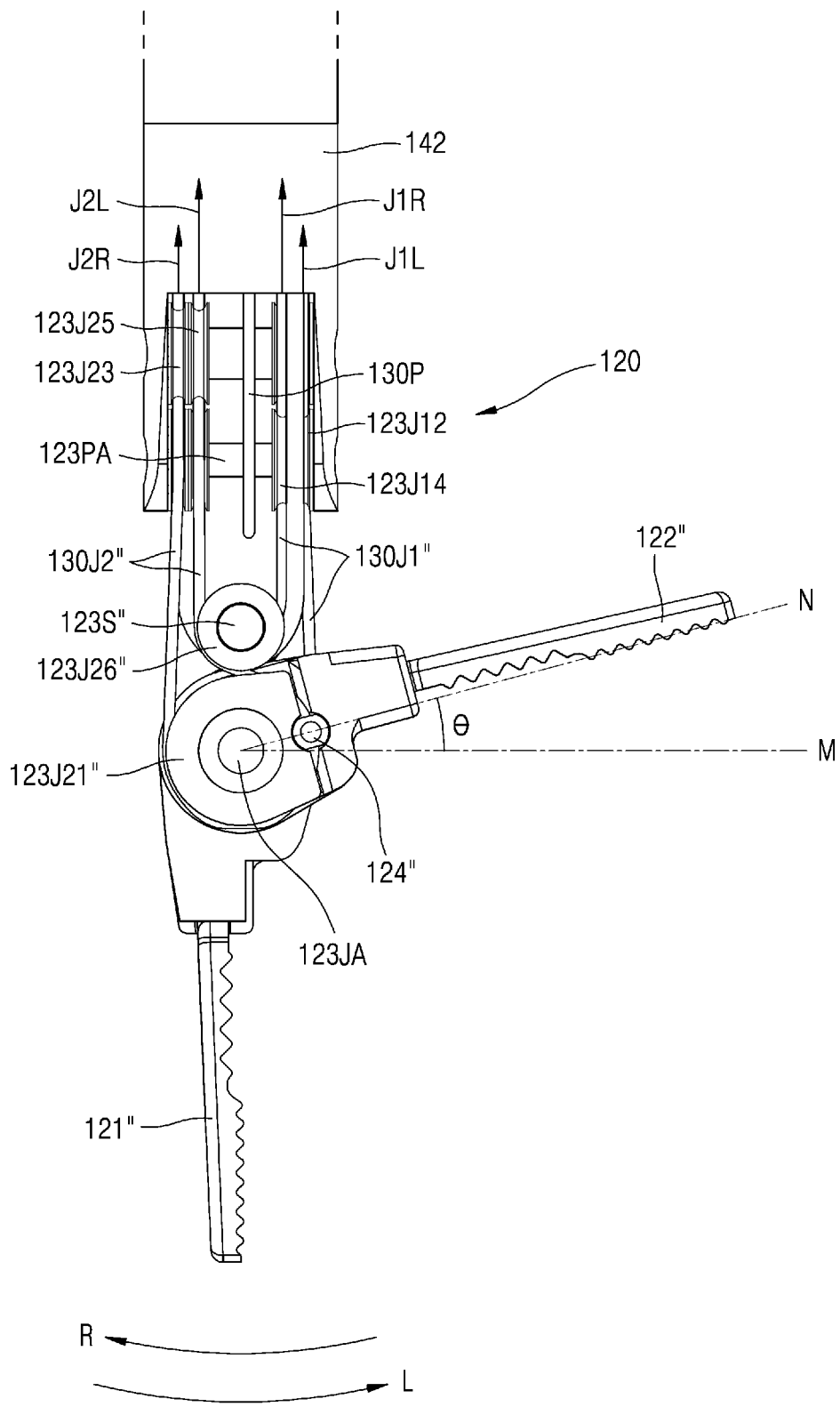
FIG. 6 is a plan view illustrating the end tool of the surgical instrument of FIG. 2.

FIGS. 4 and 5 are perspective views illustrating the end tool of the instrument for surgery shown in FIG. 2, and FIG. 6 is a plan view illustrating the end tool of the instrument for surgery shown in FIG. 2.

Referring to FIGS. 4, 5 and 6, the end the end tool 120 of the first embodiment of the present disclosure includes a pair of jaws 121 and 122, that is, a first jaw 121 and a second jaw 122 for gripping motion. In addition, the end tool 120 includes: a J11 pulley 123J11, a J12 pulley 123J12, a J13 pulley 123J13, a J14 pulley 123J14, and a J15 pulley 123J15 that are related to the rotation motion of the first jaw 121; and a J21 pulley 123J21, a J22 pulley 123J22, a J23 pulley 123J23, a J24 pulley 123J24, and a J25 pulley 123J25 that are related to the rotation motion of the second jaw 122. In this case, the first jaw 121, the J11 pulley 123J11, the J12 pulley 123J12, the J14 pulley 123J14, the second jaw 122, the J21 pulley 123J21, the J22 pulley 123J22, and the J24 pulley 123J24 may be configured to rotate around an end tool pitch rotation shaft 123PA.

In addition, A connecting part hub 142 is provided on an end portion of the connecting part 140 coupled to the end tool 120. The J12 pulley 123J12, the J13 pulley 123J13, the J14 pulley 123J14, the J15 pulley 123J15, the J22 pulley 123J22, the J23 pulley 123J23, the J24 pulley 123J24, and the J25 pulley 123J25 are connected to the connecting part hub 142.

Although it is illustrated that pulleys facing each other are parallel to each other, the idea of the present disclosure is not limited thereto. That is, the pulleys may have various positions and sizes suitable for the configuration of the end tool.

The J11 pulley 123J11 and the J21 pulley 123J21 face each other and rotate independently around a jaw rotation shaft 123JA. Here, the first jaw 121 may be fixedly coupled to the J11 pulley 123J11 so as to be rotated together with the J11 pulley 123J11, and the second jaw 122 may be fixedly coupled to the J21 pulley 123J21 so as to be rotated together with the J21 pulley 123J21. Yaw and actuation motions of the end tool 120 are performed as according to rotations of the J11 pulley 123J11 and the J21 pulley 123J21. That is, yaw motion is performed when the J11 pulley 123J11 and the J21 pulley 123J21 are rotated in the same direction, and actuation motion is performed when the J11 pulley 123J11 and the J21 pulley 123J21 are rotated in opposite directions.

In addition, a J16 pulley 123J16 and a J26 pulley 123J26 may be additionally provided as auxiliary pulleys on a side of the J11 pulley 123J11 and the J21 pulley 123J21, and the auxiliary pulleys may be rotatable on an auxiliary pulley shaft 123S. Although it is illustrated that the J16 pulley 123J16 and the J26 pulley 123J26 are configured to rotate on the single auxiliary pulley shaft 123S, the auxiliary pulleys may be configured to rotate on separate shafts, respectively. In other words, the J16 pulley 123J16 being an auxiliary pulley may be placed between the J11 pulley 123J11 and the J12 pulley 123J12/the J14 pulley 123J14. In addition, the J26 pulley 123J26 being an auxiliary pulley may be placed between the J21 pulley 123J21 and the J22 pulley 123J22/the J24 pulley 123J24. The auxiliary pulleys will be described later in more detail.

Elements related to rotation of the J11 pulley 123J11 will be described below.

The J12 pulley 123J12 and the J14 pulley 123J14 are placed to face each other at a side of the J11 pulley 123J11. In this case, the J12 pulley 123J12 and the J14 pulley 123J14 are independently rotatable about the end tool pitch rotation shaft 123PA. In addition, the J13 pulley 123J13 and the J15 pulley 123J15 are placed to face each other respectively at sides of the J12 pulley 123J12 and the J14 pulley 123J14. Here, the J13 pulley 123J13 and the J15 pulley 123J15 are independently rotatable around the Y-axis direction. Although it is illustrated that all of the J12 pulley 123J12, the J13 pulley 123J13, the J14 pulley 123J14, and the J15 pulley 123J15 are rotatable around the Y-axis direction, the idea of the present disclosure is not limited thereto, and the rotating axes of the respective pulleys may be oriented in various directions according to configurations thereof.

The first jaw wire 130J1 may be sequentially wound to make contact with at least portions of the J13 pulley 123J13, the J12 pulley 123J12, the J11 pulley 123J11, the J16 pulley 123J16, the J14 pulley 123J14, and the J15 pulley 123J15, and the first jaw wire 130J1 may move along the pulleys while rotating the pulleys.

Thus, when the first jaw wire 130J1 is pulled in the direction of an arrow J1R in FIG. 6, the first jaw wire 130J1 rotates the J15 pulley 123J15, the J14 pulley 123J14, the J16 pulley 123J16, the J11 pulley 123J11, the J12 pulley 123J12, and the J13 pulley 123J13. At this time, as the J11 pulley 123J11 is rotated in the direction of an arrow R in FIG. 6, the J11 pulley 123J11 rotates the first jaw 121.

On the other hand, when the first jaw wire 130J1 is pulled in the direction of an arrow J1L in FIG. 6, the first jaw wire 130J1 rotates the J13 pulley 123J13, the J12 pulley 123J12, the J11 pulley 123J11, the J16 pulley 123J16, the J14 pulley 123J14, and the J15 pulley 123J15. At this time, as the J11 pulley 123J11 is rotated in the direction of an arrow L in FIG. 6, the J11 pulley 123J11 rotates the first jaw 121.

Hereinafter, the auxiliary pulleys 123J16 and 123J26 will be described in more detail.

The auxiliary pulleys 123J16 and 123J26 may be in contact with the first jaw wire 130J1 and the second jaw wire 130J2, thereby changing paths of the first jaw wire 130J1 and the second jaw wire 130J2 to some degree and extending the rotation radii of the first jaw 121 and the second jaw 122. That is, according to the embodiment of the present disclosure, the auxiliary pulleys 123J16 and 123J26 are additionally provided such that the maximum rotation angle may be increased by θ as illustrated in FIG. 6. This allows the two jaws of the end tool 120 to move away from each other for actuation motion in a state in which the two jaws are rotated together by 90° in yaw motion in the direction L. That is, this is because it is possible to further rotate the second jaw 122 by an additional angle θ as illustrated in FIG. 6. Similarly, actuation motion is also possible in a state in which the two jaws are rotated in yaw motion in the direction R. In other words, owing to the auxiliary pulleys 123J16 and 123J26, the range of yaw motion in which actuation motion is possible may be increased. This will now be described in more detail.

In detail, in the instrument 100 for surgery according to the embodiment of the present disclosure, the J16 pulley 123J16 and the J26 pulley 123J26 are additionally arranged as auxiliary pulleys at a side of the J11 pulley 123J11 and the J21 pulley 123J21. In this manner, since the J16 pulley 123J16 and the J26 pulley 123J26 are arranged to change the paths of the first jaw wire 130J1 and the second jaw wire 130J2 to some degree and thus to change tangential directions of the first jaw wire 130J1 and the second jaw wire 130J2, a fixation coupling part of the second jaw wire 130J2 and the J21 pulley 123J21 may be rotated up to a line N of FIG. 6. That is, the fixation coupling part of the second jaw wire 130J2 and the J21 pulley 123J21 may be rotated until the coupling part is located on a common internal tangent of the J21 pulley 123J21 and the J26 pulley 123J26. Similarly, a coupling part of the first jaw wire 130J1 and the J11 pulley 123J11 may be rotated until the coupling part is located on an common internal tangent of the J11 pulley 123J11 and the J16 pulley 123J16, thereby extending the range of rotation in the direction R.

In this manner, according to the present disclosure, the rotation radii of the first jaw 121 and the second jaw 122 may be increased, thereby obtaining an effect of increasing the range of yaw motion in which actuation motion is normally performed for opening and closing.

Next, elements relating to the rotation of the J21 pulley 123J21 will be described.

The J22 pulley 123J22 and the J24 pulley 123J24 are placed to face each other at a side of the J21 pulley 123J21. Here, the J22 pulley 123J22 and the J24 pulley 123J24 are independently rotatable around the end tool pitch rotation shaft 123PA. In addition, the J23 pulley 123J23 and the J25 pulley 123J25 are placed to face each other at a side of the J22 pulley 123J22 and the J24 pulley 123J24. Here, the J23 pulley 123J23 and the J25 pulley 123J25 are independently rotatable around the Y-axis direction. Although it is illustrated that all of the J22 pulley 123J22, the J23 pulley 123J23, the J24 pulley 123J24, and the J25 pulley 123J25 are rotatable around the Y-axis direction, the idea of the present disclosure is not limited thereto, and the rotating axes of the respective pulleys may be oriented in various directions according to configurations thereof.

The second jaw wire 130J2 may be sequentially wound to make contact with at least portions of the J23 pulley 123J23, the J22 pulley 123J22, the J21 pulley 123J21, the J26 pulley 123J26, the J24 pulley 123J24, and the J25 pulley 123J25, and the second jaw wire 130J2 may move along the pulleys while rotating the pulleys.

Therefore, when the second jaw wire 130J2 is pulled in the direction of an arrow J2R of FIG. 6, the second jaw wire 130J2 rotates the J23 pulley 123J23, the J22 pulley 123J22, the J21 pulley 123J21, the J26 pulley 123J26, the J24 pulley 123J24, and the J25 pulley 123J25. At this time, as the J21 pulley 123J21 is rotated in the direction of the arrow R of FIG. 6, the J21 pulley 123J21 rotates the second jaw 122.

On the other hand, when the second jaw wire 130J2 is pulled in the direction of an arrow J2L of FIG. 6, the second jaw wire 130J2 rotates the J25 pulley 123J25, the J24 pulley 123J24, the J26 pulley 123J26, the J21 pulley 123J21, the J22 pulley 123J22, and the J23 pulley 123J23. At this time, as the J21 pulley 123J21 is rotated in the direction of the arrow L of FIG. 6, the J21 pulley rotates the second jaw 122.

In addition, if an end portion of the first jaw wire 130J1 is pulled in the direction of the arrow J1R of FIG. 6, and at the same time the other end portion of the first jaw wire 130J1 is pulled in the direction of the arrow J1L of FIG. 6 (that is, if both end portions of the first jaw wire 130J1 are pulled), since the first jaw wire 130J1 is wound around lower portions of the J12 pulley 123J12 and the J14 pulley 123J14 that are rotatable around the end tool pitch rotation shaft 123PA as shown in FIG. 5, the J11 pulley 123J11 to which the first jaw wire 130J1 is fixedly coupled, the first jaw 121, the jaw rotation shaft 123JA, and an end tool hub 125, and the second jaw 122 connected thereto are all rotated counterclockwise around the end tool pitch rotation shaft 123PA, and as a result, the end tool 120 is rotated downward in pitch motion. At this time, since the second jaw 122 and the second jaw wire 130J2 fixedly coupled to the second jaw 122 is wound around upper portions of the J22 pulley 123J22 and the J24 pulley 123J24 that are rotatable around the end tool pitch rotation shaft 123PA, both end portions of the second jaw wire 130J2 are respectively moved in directions opposite the directions of the arrows J2L and J2R.

In contract, if an end portion of the second jaw wire 130J2 is pulled in the direction of the arrow J2R of FIG. 6, and at the same time the other end portion of the second jaw wire 130J2 is pulled in the direction of the arrow J2L of FIG. 6, since the second jaw wire 130J2 is wound around the upper portions of the J22 pulley 123J22 and the J24 pulley 123J24 that are rotatable around the end tool pitch rotation shaft 123PA as shown in FIG. 5, the J21 pulley 123J21 to which the second jaw wire 130J1 is fixedly coupled, the second jaw 122, the jaw rotation shaft 123JA, and the end tool hub 125, and the first jaw 121 connected thereto are all rotated clockwise around the end tool pitch rotation shaft 123PA, and as a result, the end tool 120 is rotated upward in pitch motion. At this time, since the first jaw 121 and the first jaw wire 130J1 fixedly coupled to the first jaw 121 are wound around the lower portions of the J12 pulley 123J12 and the J14 pulley 123J14 that are rotatable around the end tool pitch rotation shaft 123PA, both end portions of the first jaw wire 130J1 are respectively moved in directions opposite the directions of the arrows J1L and J1R.

In addition, the end tool 120 of the instrument 100b for surgery may further include a pitch pulley 123P, the manipulation part 110 may further include a pitch wire end pulley 115P, and the power transmission part 130 may further include the pitch wire 130P. In detail, the pitch pulley 123P of the end tool 120 may be rotatable about the end tool pitch rotation shaft 123PA and may be fixedly coupled to the end tool hub 125. In addition, a pitch pulley of the manipulation part may be rotatable about a pitch rotation shaft and may be fixedly coupled to a pitch manipulation part (not shown). In addition, the pitch wire 130P may connect the pitch pulley 123P of the end tool 120 to the pitch pulley of the manipulation part.

Thus, if a user rotates a first handle 114 around a pitch rotation shaft 1111 while holding the first handle 114 of the manipulation part 110, a pitch pulley coupled to the first handle 114 is rotated around the pitch rotation shaft 1111, and the rotation of the pitch pulley is transmitted to the pitch pulley 123P of the end tool 120 through the pitch wire 130P to rotate the pitch pulley 123P. As a result, the end tool 120 is rotated, and a pitch motion is performed.

That is, since the instrument 100 for surgery according to the first embodiment of the present disclosure includes the pitch pulley 123P of the end tool 120, the pitch wire end pulley 115P of the manipulation part 110, and the pitch wire 130P of the power transmission part 130, a pitch motion driving force of the pitch manipulation part 111 may be more completely transmitted to the end tool 120, and thus reliability of motion may be improved.

Although FIG. 4 shows that the pitch pulley 123P is integrally formed with the end tool hub 125 as one body, the inventive concept of the present invention is not limited thereto. In an embodiment, the pitch pulley 123P and the end tool hub 125 may be formed as separate elements, which are axially coupled to each other.

(Manipulation Part)

Figure 7:
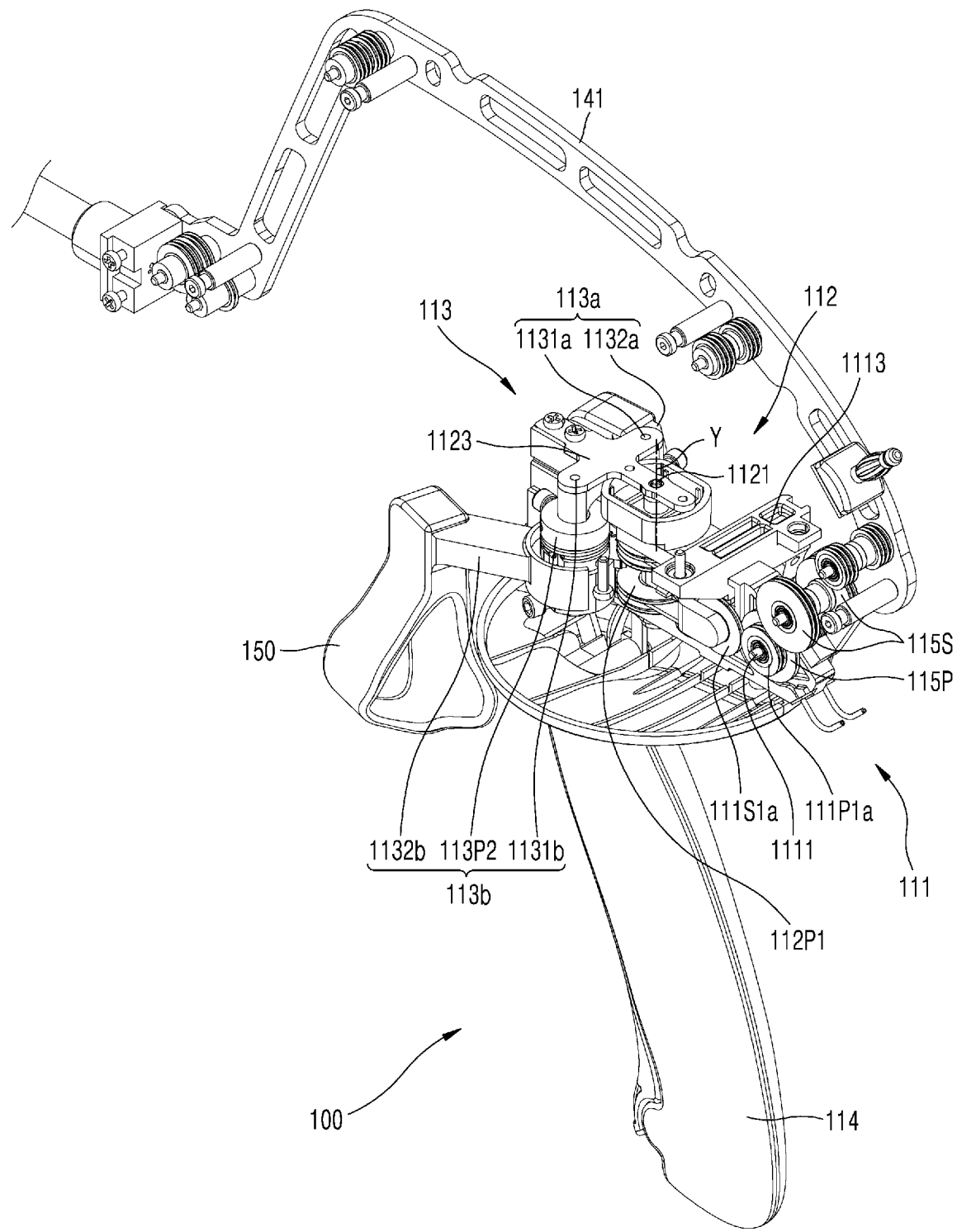
FIGS. 7 and 8 are perspective views illustrating a manipulation portion of the surgical instrument of FIG. 2.
Figure 8:
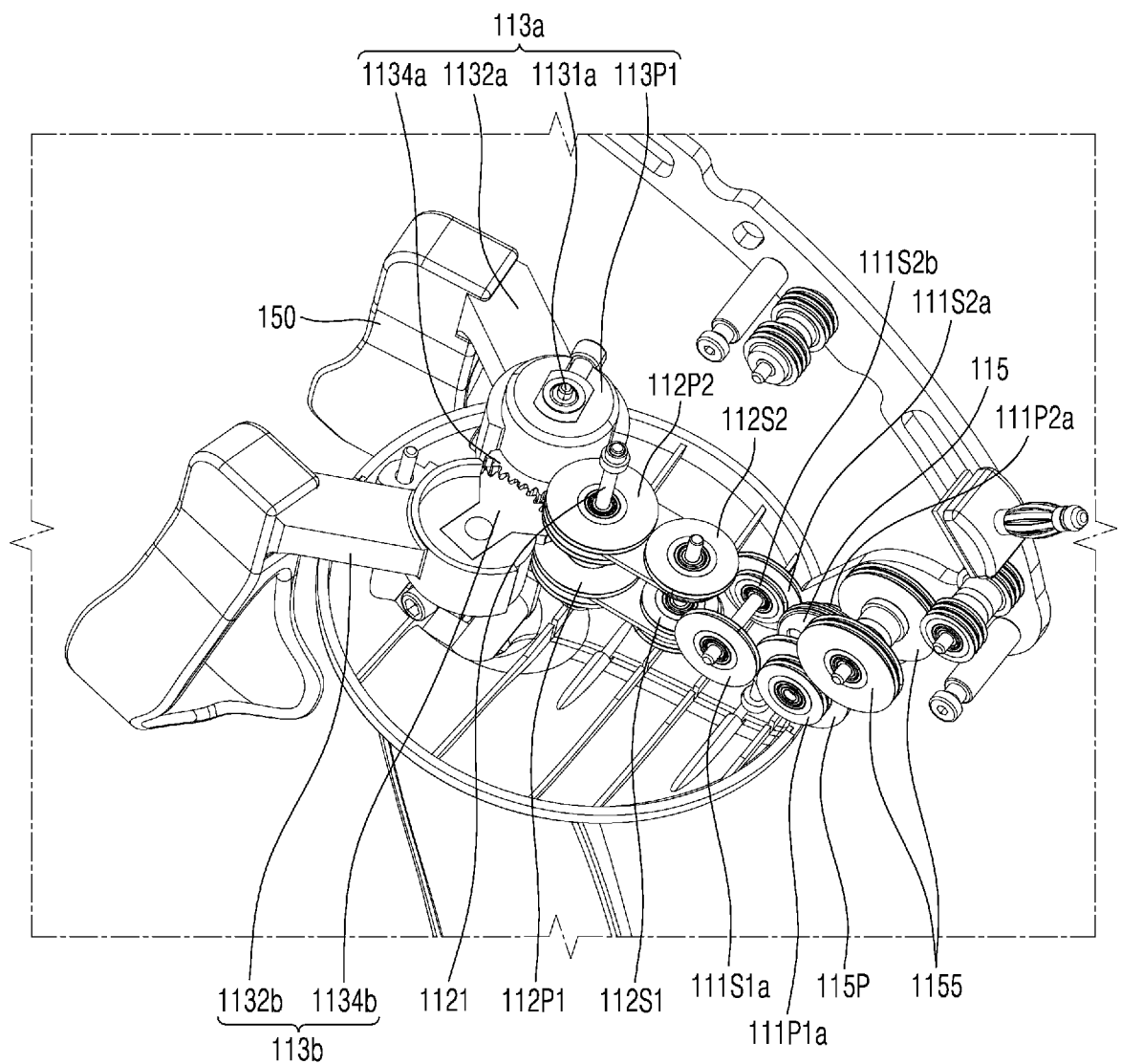

FIG. 7 and FIG. 8 are a perspective view illustrating the manipulation part of the instrument for surgery shown in FIG. 2.

Referring to FIG. 2 to FIG. 8, the manipulation part 110 of the instrument 100 for surgery includes the first handle 114 which a user may grip, the actuation manipulation part 113 configured to control actuation motion of the end tool 120, the yaw manipulation part 112 configured to control yaw motion of the end tool 120, and the pitch manipulation part 111 configured to control pitch motion of the end tool 120. In addition, the manipulation part 110 further includes the ring handle 150.

First, an example operation of the instrument 100 for surgery shown in FIG. 2 will be described. In a state in which a user holds the first handle 114 with his/her palm, the user may perform a pitch motion by rotating the first handle 114 around the Y axis (that is, around the pitch rotation shaft 1111) and a yaw motion by rotating the first handle 114 around the Z axis (that is, around a yaw rotation shaft 1121). In addition, in a state in which the user inserts his/her thumb and index finger in the ring handle 150 formed on an end of the actuation manipulation part 113, the user may rotate the actuation manipulation part 113 to perform an actuation motion.

Here, when the manipulation part 110 of the instrument 100 for surgery is rotated in a direction with respect to the connecting part 140, the end tool 120 is rotated intuitively in the same direction as the direction in which the manipulation part 110 is manipulated. In other words, if the first handle 114 of the manipulation part 110 is rotated in a certain direction, the end tool 120 is also rotated intuitively in the same direction as the certain direction, and thus a pitch motion or a yaw motion is performed. Here, the expression "intuitively in the same direction" may be used to denote that the direction in which a finger of a user holding the manipulation part 110 is moved is substantially the same as the direction in which a distal end portion of the end tool 120 is moved. The expression "intuitively in same direction" may not refer to completely in the same direction in a three-dimensional coordinate system. For example, it may be understood that the expression refers to sameness to the following extend: if a finger of a user is moved leftward, the distal end portion of the end tool 120 is also be moved leftward, and if the finger of the user is moved downward, the distal end portion of the end tool 120 is also moved downward.

To this end, in the instrument 100 for surgery of the first embodiment of the present disclosure, the manipulation part 110 and the end tool 120 are provided in the same direction with respect to a plane perpendicular to an extension axis (the X axis) of the connecting part 140. That is, when viewed based on a YZ plane of FIG. 2, the manipulation part 110 extends in a positive (+) X-axis direction, and the end tool 120 also extends in the positive (+) X-axis direction. In other words, it may be stated that the formation direction of the end tool 120 on an end portion of the connecting part 140 is the same as the formation direction of the manipulation part 110 on the other end portion of the connecting part 140 based on the YZ plane. Furthermore, in other words, it may be stated that the manipulation part 110 is located in a direction away from the body of a user holding the manipulation part 110, that is, in a direction in which the end tool 120 is provided. That is, in the case of parts such as the first handle 114 and actuation rotation parts 1132a and 1132b which a user holds and moves for actuation, yaw, and pitch motions, each moving portion extends from the rotation center of a corresponding joint for the motions in the positive (+) X-axis direction. In this manner, the manipulation part 110 may be configured like the end tool 120 in which each moving portion extends from the rotation center of a corresponding joint for the motions in the positive (+) X-axis direction, and as described with reference to FIG. 1, a manipulation direction of a user may be identical to an operation direction of the end tool from the viewpoint of rotation directions and leftward and rightward directions. As a result, intuitively the same manipulation may be performed.

In detail, in the case of an instrument for surgery of the related art, a direction in which a user manipulates a manipulation part is different from a direction in which the end tool is actually operated, that is, intuitively different from the direction in which the end tool is actually operated. Thus, surgeons may not easily intuitively manipulate the instrument for surgery and may spend a long time to learn a skill of operating the end tool in desired directions. In some cases, patients may suffer from malfunctions.

In order to solve such problems, the instrument 100 for surgery of the first embodiment of the present disclosure is configured such that the manipulation direction of the manipulation part 110 and the operation direction of the end tool 120 are intuitively identical to each other. To this end, the manipulation part 110 is configured like the end tool 120. That is, in the manipulation part 110, portions that are actually moved for actuation, yaw, and pitch motions extend respectively from rotation centers of corresponding joints in the positive (+) X-axis direction. This will now be described in more detail.

The first handle 114 may be configured such that a user may grip the first handle 114 with his/her hand. In particular, a user may grip the first handle 114 by holding around the first handle 114 with his/her palm. In addition, the actuation manipulation part 113 and the yaw manipulation part 112 are provided above the first handle 114, and the pitch manipulation part 111 is provided at a side of the yaw manipulation part 112. In addition, another end portion of the pitch manipulation part 111 is connected to the bent part 141 of the connecting part 140.

The actuation manipulation part 113 includes a first actuation manipulation part 113a and a second actuation manipulation part 113b. The first actuation manipulation part 113a includes a first actuation rotation shaft 1131a, a first actuation rotation part 1132a, a first actuation pulley 113P1, and a first actuation gear 1134a. The second actuation manipulation part 113b includes a second actuation rotation shaft 1131b, a second actuation rotation part 1132b, a second actuation pulley 113P2, and a second actuation gear 1134b. Here, the ring handle 150 may be further formed on ends of the first and second actuation rotation parts 1132a and 1132b and may function as second handles.

Here, the actuation rotation shafts 1131a and 1131b may make a predetermined angle with an XY plane on which the connecting part 140 is located. For example, the actuation rotation shafts 1131a and 1131b may be parallel with the Z axis. In this state, if the pitch manipulation part 111 or the yaw manipulation part 112 is rotated, the coordinate system of the actuation manipulation part 113 may be relatively varied. However, the idea of the present disclosure is not limited thereto, and the actuation rotation shafts 1131a and 1131b may be oriented in various directions according to ergonomic designs for the hand structure of a user holding the actuation manipulation part 113.

In addition, the first actuation rotation part 1132a, the first actuation pulley 113P1, and the first actuation gear 1134a may be fixedly coupled to each other so as to be rotated together around the first actuation rotation shaft 1131a. Here, the first actuation pulley 113P1 may include a single pulley or two pulleys fixedly coupled to each other.

Similarly, the second actuation rotation part 1132b, the second actuation pulley 113P2, and the second actuation gear 1134b may be fixedly coupled to each other so as to be rotated together around the second actuation rotation shaft 1131b. Here, the second actuation pulley 113P2 may include a single pulley or two pulleys fixedly coupled to each other.

Here, the first actuation gear 1134a and the second actuation gear 1134b may be engaged with each other, and thus if one of the first and second actuation gears 1134a and 1134b is rotated, the first and second actuation gears 1134a and 1134b may be rotated together in opposite directions.

The yaw manipulation part 112 may include a yaw rotation shaft 1121, a first jaw yaw pulley 112P1, a second jaw yaw pulley 112P2, and a yaw frame 1123. In addition, the yaw manipulation part 112 may further include a first jaw yaw auxiliary pulley 112S1 provided on a side of the first jaw yaw pulley 112P1, and a second jaw yaw auxiliary pulley 112S2 provided on a side of the second jaw yaw pulley 112P2. Here, the first jaw yaw auxiliary pulley 112S1 and the second jaw yaw auxiliary pulley 112S2 may be coupled to a pitch frame 1113 (described later). In the drawings, it is illustrated that the yaw manipulation part 112 includes the first jaw yaw pulley 112P1 and the second jaw yaw pulley 112P2, and each of the first jaw yaw pulley 112P1 and the second jaw yaw pulley 112P2 includes two pulleys facing each other and independently rotatable. However, the idea of the present disclosure is not limited thereto. That is, according to the configuration of the yaw manipulation part 112, the yaw manipulation part 112 may include one or more pulleys having the same diameter or different diameters.

Specifically, the yaw rotation shaft 1121 is provided on a side of the actuation manipulation part 113 above the first handle 114. In this case, the first handle 114 is rotatable around the yaw rotation shaft 1121.

Here, the yaw rotation shaft 1121 may make a predetermined angle with the XY plane in which the connecting part 140 is provided. For example, the yaw rotation shaft 1121 may be oriented in a direction parallel to the Z axis, and in this state, if the pitch manipulation part 111 is rotated, the coordinate system of the yaw rotation shaft 1121 may be relatively varied as described above. However, the idea of the present disclosure is not limited thereto, and the yaw rotation shaft 1121 may be oriented in various directions according to ergonomic designs for the hand structure of a user holding the manipulation part 110.

In addition, the first jaw yaw pulley 112P1 and the second jaw yaw pulley 112P2 are coupled to the yaw rotation shaft 1121 such that the first jaw yaw pulley 112P1 and the second jaw yaw pulley 112P2 may be rotated on the yaw rotation shaft 1121. In addition, the first jaw wire 130J1 may be wound around the first jaw yaw pulley 112P1, and the second jaw wire 130J2 may be wound around the second jaw yaw pulley 112P2. In this case, each of the first jaw yaw pulley 112P1 and the second jaw yaw pulley 112P2 may include two pulleys facing each other and independently rotatable. Therefore, an inward wire and an outward wire may be respectively wound around separate pulleys and thus may not interfere with each other.

The yaw frame 1123 connects the first handle 114, the yaw rotation shaft 1121, the first actuation rotation shaft 1131a, and the second actuation rotation shaft 1311b such that the first handle 114, the yaw manipulation part 112, and the actuation manipulation part 113 may be rotated together around the yaw rotation shaft 1121.

The pitch manipulation part 111 may include the pitch rotation shaft 1111, a first jaw pitch pulley-a 1111P1a, a first jaw pitch pulley-b 111P1b, a second jaw pitch pulley-a 111P2a, a second jaw pitch pulley-b 111P2b, and the pitch frame 1113. In addition, the pitch manipulation part 111 may further include a first jaw pitch auxiliary pulley-a 111S1a provided at a side of the first jaw pitch pulley-a 111P1a, a first jaw pitch auxiliary pulley-b 111S1b provided at a side of the first jaw pitch pulley-b 111P1b, a second jaw pitch auxiliary pulley-a 111S2a provided at a side of the second jaw pitch pulley-a 111P2a, and a second jaw pitch auxiliary pulley-b 111S2b provided at a side of the second jaw pitch pulley-b 111P2b. The pitch manipulation part 111 is connected to a bent part 141 of a connecting part 140 through the pitch rotation shaft 1111.

In detail, the pitch frame 1113 serves as a base frame of the pitch manipulation part 111, and the yaw rotation shaft 1121 is rotatably coupled to an end portion of the pitch frame 1113. That is, the yaw frame 1123 is rotatable around the yaw rotation shaft 1121 with respect to the pitch frame 1113.

As described above, the yaw frame 1123 connects the first handle 114, the yaw rotation shaft 1121, the first actuation rotation shaft 1131a, and the second actuation rotation shaft 1311b to each other, and is also connected to the pitch frame 1113. Therefore, if the pitch frame 1113 is rotated around the pitch rotation shaft 1111, the yaw frame 1123, the first handle 114, the yaw rotation shaft 1121, the first actuation rotation shaft 1131a, and the second actuation rotation shaft 1311b connected to the pitch frame 1113 are rotated together. That is, if the pitch manipulation part 111 is rotated around the pitch rotation shafts 1111, the actuation manipulation part 113 and the yaw manipulation part 112 are rotated together with the pitch manipulation part 111. In other words, if a user rotates the first handle 114 around the pitch rotation shaft 1111, the actuation manipulation part 113, the yaw manipulation part 112, and the pitch manipulation part 111 are moved together.

The pitch manipulation part 111, the first jaw pitch pulley-a 111P1a, the first jaw pitch pulley-b 111P1b, the second jaw pitch pulley-a 111P2a, and the second jaw pitch pulley-b 111P2b are coupled to the pitch frame 1113. In this case, the first jaw pitch pulley-a 111P1a, the first jaw pitch pulley-b 111P1b, the second jaw pitch pulley-a 111P2a, and the second jaw pitch pulley-b 111P2b are coupled to the pitch rotation shaft 1111 in a manner rotatable around the pitch rotation shaft 1111.

Here, the first jaw pitch pulley-a 111P1a and the first jaw pitch pulley-b 111P1b may face each other and may be independently rotated. Therefore, an inward wire and an outward wire may be respectively wound around separate pulleys and thus may not interfere with each other. Similarly, the second jaw pitch pulley-a 111P2a and the second jaw pitch pulley-b 111P2b may face each other and may be independently rotated. Therefore, an inward wire and an outward wire may be respectively wound around separate pulleys and thus may not interfere with each other.

Referring to FIG. 7, the pitch wire end pulley 115P is fixedly coupled to the pitch frame 1113 and rotatable together with the pitch frame 1113. In addition, the pitch wire 130P is fixedly coupled to the pitch frame 1113 through a pitch wire auxiliary pulley 115S and the pitch wire end pulley 115P. As a result, the pitch frame 1113 and the pitch wire end pulley 115P may be rotated together around the pitch rotation shaft 1111 by pitch rotation.

The pitch wire 130P is operated as follows.

The pitch pulley 123P is fixedly coupled to the end tool hub 125 of the end tool 120, and the manipulation part 110 includes the pitch wire end pulley 115P, wherein the pitch pulley 123P and the pitch wire end pulley 115P are connected to each other through the pitch wire 130P such that pitch motion of the end tool 120 may be easily performed by pitch-manipulating the manipulation part 110. Here, both ends of the pitch wire 130P are fixedly coupled to the pitch frame 1113 respectively through the pitch wire auxiliary pulley 115S and the pitch wire end pulley 115P, and the pitch wire end pulley 115P is also fixedly coupled to the pitch frame 1113. That is, the pitch frame 1113 and the pitch wire end pulley 115P are rotated together about the pitch rotation shaft 1111 by pitch rotation of the manipulation part, and as a result, both sides of the pitch wire 130P are also moved in opposite directions such that additional power for pitch rotation may be transmitted independently of pitch motion of the end tool by the first jaw wire 130J1 and the second jaw wire 130J2.

The first handle 114, the pitch manipulation part 111, the yaw manipulation part 112, and the actuation manipulation part 113 are connected as follows. The actuation rotation shafts 1131a and 1131b, the yaw rotation shaft 1121, and the pitch rotation shaft 1111 may be provided on the first handle 114. In this case, since the actuation rotation shafts 1131a and 1131b are directly provided on the first handle 114, and the first handle 114 and the actuation manipulation part 113 may be directly connected to each other. In addition, since the yaw rotation shaft 1121 is directly provided on the first handle 114, the first handle 114 and the yaw manipulation part 112 may be directly connected to each other. However, since the pitch manipulation part 111 is provided at a side of the yaw manipulation part 112 and connected to the yaw manipulation part 112, the pitch manipulation part 111 may not be directly connected to the first handle 114 but may be indirectly connected to the first handle 114 through the yaw manipulation part 112.

Referring to the drawings, in the instrument 100 for surgery according to the first embodiment of the present disclosure, the pitch manipulation part 111 and the end tool 120 may be provided on the same axis or on parallel axes (to the X axis). That is, the pitch rotation shaft 1111 of the pitch manipulation part 111 is provided on an end portion of the bent part 141 of the connecting part 140, and the end tool 120 is provided on the other end portion of the connecting part 140.

In addition, one or more relay pulleys MP may be placed on a middle portion of the connecting part 140, particularly, on the bent part 141 of the connecting part 140 to change paths of wires or guide wires. At least portions of wires may be wound around the relay pulleys MP, thereby guiding paths of the wires and arranging the wires along a bent shape of the bent part 141. In the drawings, it is illustrated that the connecting part 140 includes the bent part 141 and has a curved shape with a predetermined radius of curvature. However, the idea of the present disclosure is not limited thereto. If necessary, the connecting part 140 may have a straight shape or may be bent at least one time, and even in this case, it may be stated that the pitch manipulation part 111 and the end tool 120 are provided substantially on the same axis or parallel axes. In addition, although FIG. 3 illustrates that the pitch manipulation part 111 and the end tool 120 are provided on an axis parallel to the X axis, the idea of the present disclosure is not limited thereto. For example, the pitch manipulation part 111 and the end tool 120 may be provided on different axes.

(Actuation Motion, Yaw Motion, Pitch Motion)

Actuation motion, yaw motion, and pitch motion in this embodiment will be described as follows.

First, the actuation motion is as follows.

When a user rotates actuation rotating portions 1132a and 1132b using one or both of an index finger inserted into a hand ring 150 connected to a first actuation rotating portion 1132a and a thumb inserted into a hand ring 150 connected to a second actuation rotating portion 1132b, a first actuation pulley 113P1 fixedly coupled to the first actuation rotating portion 1132a and a first actuation gear 1134a are rotated around a first actuation rotation shaft 1131a, and a second actuation pulley 113P2 fixedly coupled to the second actuation rotating portion 1132b and a second actuation gear 1134b are rotated around a second actuation rotation shaft 1311b. At this time, as the first actuation pulley 113P1 and the second actuation pulley 113P2 rotate in opposite directions, a first jaw wire 130J1 having one end fixedly coupled to and wound on the first actuation pulley 113P1 and a second jaw wire 130J2 having one end fixedly coupled to and wound on the second actuation pulley 113P2 also move in opposite directions. And, this rotational force is transmitted to an end tool 120 through a power transmission portion 130, two jaws 121 and 122 of the end tool 120 perform the actuation motion.

Here, the actuation motion refers to an action of opening or closing the jaws 121 and 122 while the two jaws 121 and 122 rotate in opposite directions to each other, as described above. That is, when the actuation rotating portions 1132a and 1132b of an actuation manipulation portion 113 are rotated in a direction closer to each other, a first jaw 121 rotates counterclockwise and a second jaw 122 rotates clockwise to close the end tool 120, but when the actuation rotating portions 1132a and 1132b of the actuation manipulation portion 113 are rotated in a direction away from each other, the first jaw 121 rotates clockwise and the second jaw 122 rotates counterclockwise to open the end tool 120. In this embodiment, for the above-described actuation manipulation, the first actuation rotating portion 1132a and the second actuation rotating portion 1132b were provided to constitute a second handle, and two fingers were gripped to enable manipulation. However, unlike the above, the actuation manipulation portion 113 for actuation manipulation to open and close the two jaws of the end tool 120 with each other may be configured differently so that, for example, two actuation pulleys (first actuation pulley 113P1, second actuation pulley 113P2) operate opposite to each other by one actuation rotating portion.

Next, the yaw motion is as follows.

When the user rotates a first handle 114 around a yaw rotation shaft 1121 while holding the first handle 114, the actuation manipulation portion 113 and a yaw manipulation portion 112 make yaw rotation around the yaw rotation shaft 1121. That is, when the first actuation pulley 113P1 of a first actuation manipulation portion 113a fixedly coupled to the first jaw wire 130J1 rotates around the yaw rotation shaft 1121, the first jaw wire 130J1 wound on a first jaw yaw pulley 112P1 moves. Similarly, when the second actuation pulley 113P2 of a second actuation manipulation portion 113b fixedly coupled to the second jaw wire 130J2 rotates around the yaw rotation shaft 1121, the second jaw wire 130J2 wound around a second jaw yaw pulley 112P2 moves. At this time, the first jaw wire 130J1 connected to the first jaw 121 and the second jaw wire 130J2 connected to the second jaw 122 are wound around the first jaw yaw pulley 112P1 and the second jaw yaw pulley 112P2, so that the first jaw 121 and the second jaw 122 rotate in the same direction during yaw rotation. And, this rotational force is transmitted to the end tool 120 through the power transmission portion 130, the two jaws 121 and 122 of the end tool 120 performs the yaw motion that rotates in the same direction.

At this time, since a yaw frame 1123 connects the first handle 114, yaw rotation shaft 1121, first actuation rotation shaft 1131a and second actuation rotation shaft 1131b, first handle 114, yaw manipulation portion 112 and actuation manipulation portion 113 are rotated together around the yaw rotation shaft 1121.

Next, the pitch motion is as follows.

When the user rotates the first handle 114 around a pitch rotation shaft 1111 while holding the first handle 114, the actuation manipulation portion 113, the yaw manipulation portion 112 and a pitch manipulation portion 111 make pitch rotation around the pitch rotation shaft 1111. That is, when the first actuation pulley 113P1 of the first actuation manipulation portion 113a fixedly coupled to the first jaw wire 130J1 rotates around the pitch rotation shaft 1111, the first jaw wire 130J1 wound on a first jaw pitch pulley-a 111P1a and a first jaw pitch pulley-b 111P1b moves. Similarly, when the second actuation pulley 113P2 of the second actuation manipulation portion 113b fixedly coupled to the second jaw wire 130J2 rotates around the pitch rotation shaft 1111, the second jaw wire 130J2 wound on a second jaw pitch pulley-a 111P2a and a second jaw pitch pulley-b 111P2b moves. At this time, the first jaw wire 130J1 and the second jaw wire 130J2 are wound on a first jaw pitch pulley 111P1a, 111P1b and a second jaw pitch pulley 111P2a, 111P2b, so that, as described through FIG. 5, both strands of the first jaw wire 130J1 move in the same direction, and both strands of the second jaw wire 130J2 move in the same direction, thus the first jaw 121 and second jaw 122 may perform pitch rotation. And, this rotational force is transmitted to the end tool 120 through the power transmission portion 130, so that the two jaws 121 and 122 of the end tool 120 performs a pitch motion.

At this time, when a pitch frame 1113 rotates around the pitch rotation shaft 1111, the yaw frame 1123 connected to the pitch frame 1113, first handle 114, yaw rotation shaft 1121, first actuation rotation shaft 1131a and second actuation rotation shaft 1311b rotate together because the pitch frame 1113 is connected to the yaw frame 1123, and the yaw frame 1123 connects the first handle 114, the yaw rotation shaft 1121, the first actuation rotation shaft 1131a and the second actuation rotation shaft 1311b. That is, when the pitch manipulation portion 111 rotates around the pitch rotation shaft 1111, the actuation manipulation portion 113 and the yaw manipulation portion 112 are rotated together with the pitch manipulation portion 111.

In summary, in a surgical instrument 100 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 120 is induced. Furthermore, auxiliary pulleys may be formed on one side of each pulley, and the wire may not be wound several times on one pulley by these auxiliary pulleys.

Accordingly, as illustrated in FIG. 7 illustrating a first embodiment, the actuation operation, the yaw operation, and the pitch operation may be performed independently of each other.

As described through FIG. 1, the actuation manipulation portion 113, yaw manipulation portion 112, and pitch manipulation portion 111 have their own rotation shafts located at the back of each manipulation portion, so it is configured the same as the joint configuration of the end tool, allowing the user to perform intuitively matching operations.

Especially, in a surgical instrument 100 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 120 is induced. Furthermore, auxiliary pulleys may be formed on one side of each pulley, and the wire may not be wound several times on one pulley by these auxiliary pulleys, so that the wires wound on the pulley do not come into contact with each other, and the path of the wire that goes into the pulley and the wire that comes out is also formed safely, so the safety and efficiency of power transmission of the wire may be improved.

On the other hand, as described above, the yaw manipulation portion 112 and the actuation manipulation portion 113 are formed directly on the first handle 114. Therefore, when the first handle 114 rotates around the pitch rotation shaft 111I, the yaw manipulation portion 112 and the actuation manipulation portion 113 also rotate together with the first handle 114. Due to this, a coordinate system of the yaw manipulation portion 112 and the actuation manipulation portion 113 is not fixed, but continues to change relatively according to the rotation of the first handle 114. That is, in FIG. 2 and the like, the yaw manipulation portion 112 and the actuation manipulation portion 113 are illustrated as being parallel to a Z-axis. However, when the first handle 114 is rotated, the yaw manipulation portion 112 and the actuation manipulation portion 113 are not parallel to the Z-axis. That is, the coordinate system of the yaw manipulation portion 112 and the actuation manipulation portion 113 is changed according to the rotation of the first handle 114. However, in the present specification, for convenience of explanation, if there is no separate explanation, the coordinate system of the yaw manipulation portion 112 and the actuation manipulation portion 113 was described based on a state in which the first handle 114 is positioned vertically with respect to the connection portion 140 as illustrated in FIG. 2.

(End Tool Pulley Assembly)

Hereinafter, an end tool pulley assembly constituting a part of the end tool will be described in more detail.

Figure 9:
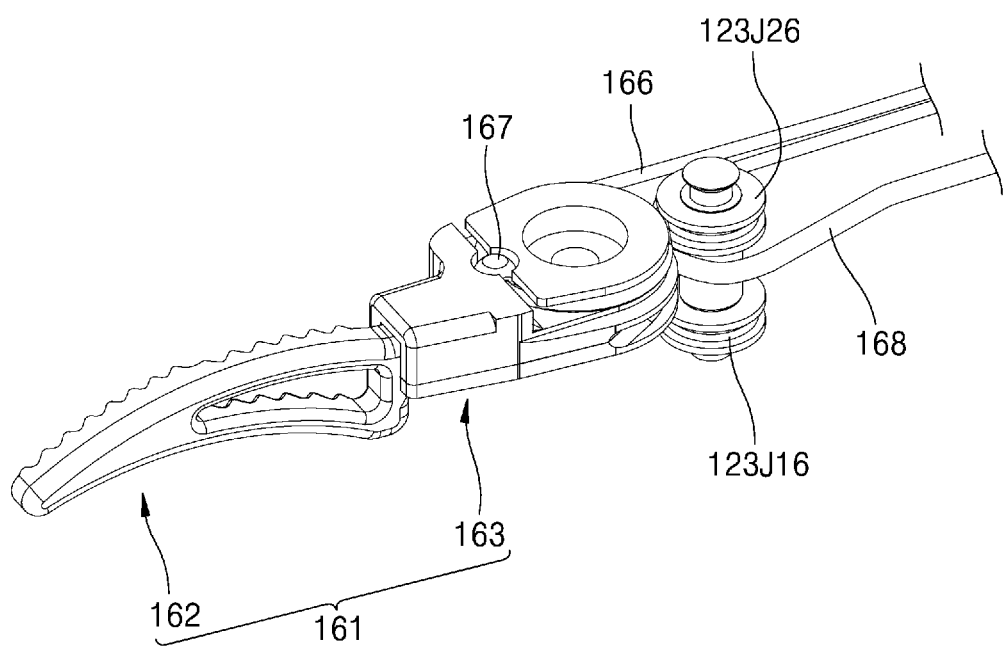
FIG. 9 is a perspective view of an end tool pulley assembly.
Figure 10:
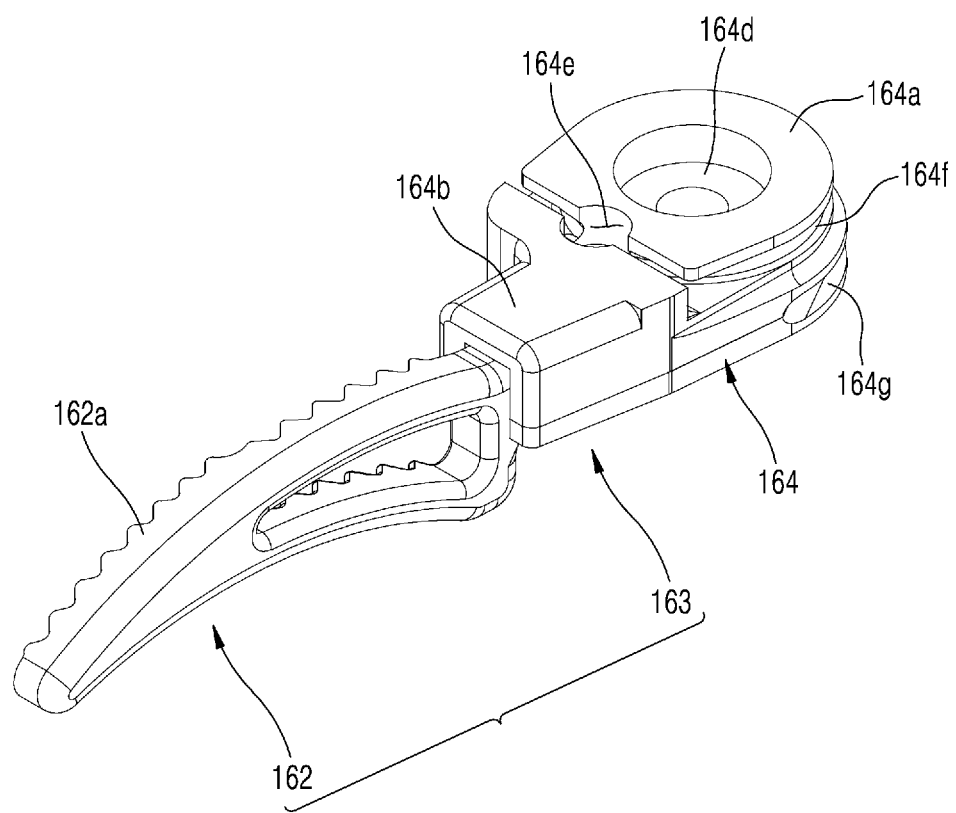
FIG. 10 is a perspective view illustrating a state in which the wire and the electric wire are removed from the end tool pulley assembly of FIG. 9.
Figure 11:
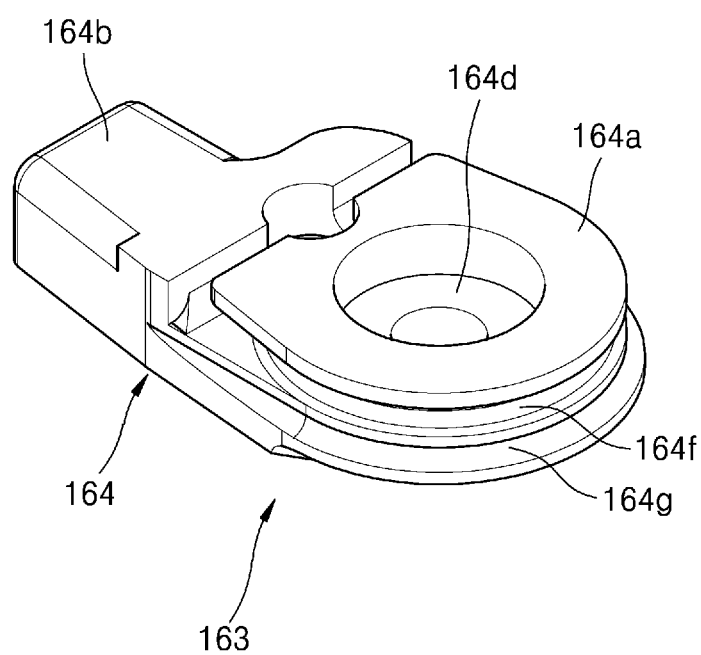
FIG. 11 is a perspective view of an end tool pulley of the end tool pulley assembly of FIG. 9.
Figure 12:
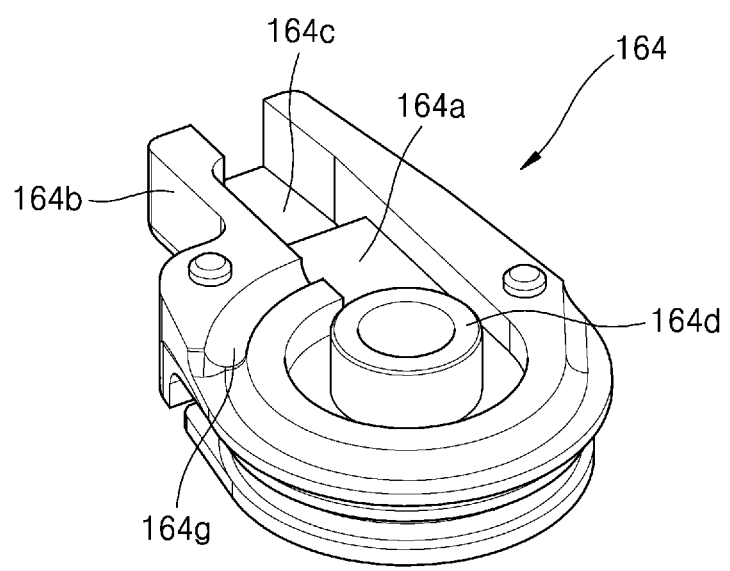
FIG. 12 is a bottom perspective view of an upper plate of the end tool pulley of FIG. 11.
Figure 13:
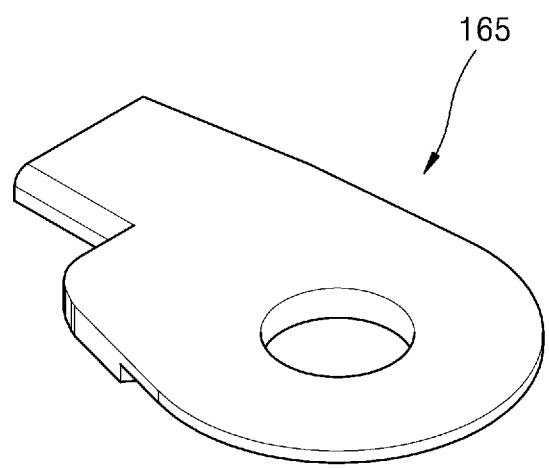
FIG. 13 is a perspective view of a lower plate of the end tool pulley of FIG. 11.
Figure 14:
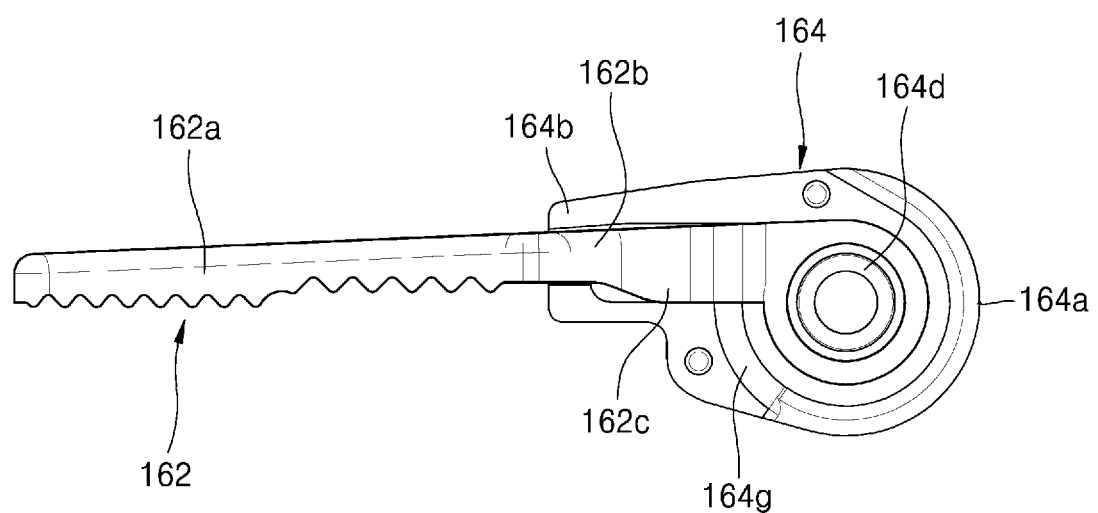
FIG. 14 is a bottom view of a state in which the lower plate is removed from the end tool pulley assembly of FIG. 10.
Figure 15:
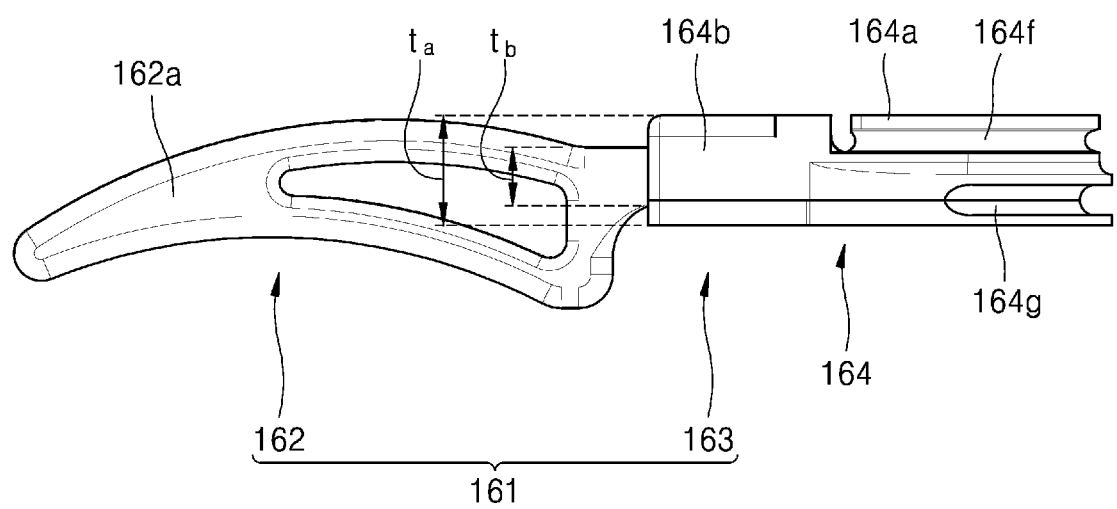
FIG. 15 is a side view of the end tool pulley assembly of FIG. 10.
Figure 16:
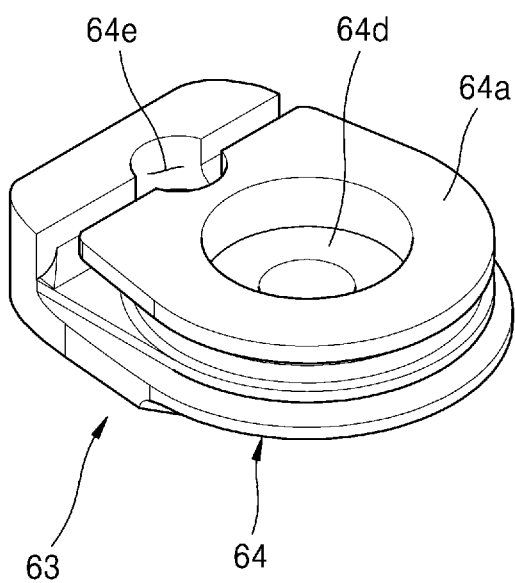
FIGS. 16 to 20 are views illustrating an end tool pulley assembly used in the prior art.
Figure 17:
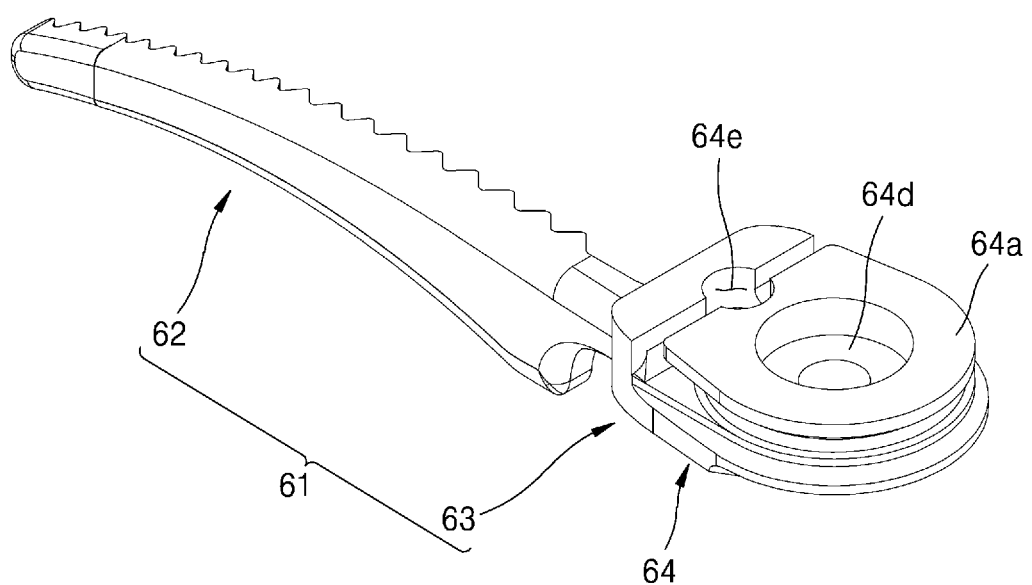

FIG. 9 is a perspective view of an end tool pulley assembly. FIG. 10 is a perspective view illustrating a state in which the wire and the electric wire are removed from the end tool pulley assembly of FIG. 9. FIG. 11 is a perspective view of an end tool pulley of the end tool pulley assembly of FIG. 9. FIG. 12 is a bottom perspective view of an upper plate of the end tool pulley of FIG. 11. FIG. 13 is a perspective view of a lower plate of the end tool pulley of FIG. 11. FIG. 14 is a bottom view of a state in which the lower plate is removed from the end tool pulley assembly of FIG. 10. FIG. 15 is a side view of the end tool pulley assembly of FIG. 10.

Here, a jaw 162 of FIG. 9 may be the first jaw 121 or the second jaw 122 of FIG. 5. In addition, an end tool pulley 163 of FIG. 9 may be a J11 pulley 123J11 or a J21 pulley 123J21 of FIG. 5. In addition, a wire 166 of FIG. 9 may be the first jaw wire 130J1 or the second jaw wire 130J2 of FIG. 5. In addition, a fixed coupling portion 167 of the wire 166 of FIG. 9 may be a fixed coupling portion 124 of the first jaw wire 130J1 or the second jaw wire 130J2 of FIG. 6.

Referring to FIGS. 9 to 15, an end tool pulley assembly 161 according to the present disclosure may include the jaw 162 and the end tool pulley 163. And, the end tool pulley 163 may include an upper plate 164 and a lower plate 165.

The fixed coupling portion 167 is formed in any one region of the wire 166, and the fixed coupling portion 167 is inserted into a wire coupling groove 164e to be described later of the end tool pulley 163, so that the wire 166 is fixedly coupled to the end tool pulley 163. In this way, as the wire 166 and the end tool pulley 163 are fixedly coupled, when the wire 166 is pulled in one direction, the end tool pulley 163 rotates. Meanwhile, although the fixed coupling portion 167 is illustrated as having a ball shape in the drawings, the spirit of the present disclosure is not limited thereto, and may be formed in various shapes such as a tube. Here, the wire 166 passes through the connection portion (see 140 of FIG. 2) and is connected to the manipulation portion (see 110 of FIG. 2), and controls at least part of the pitch/yaw/actuation movement of the end tool (see 120 of FIG. 2).

An electric wire 168 is connected to the jaw 162 and is formed to pass through the inside of the end tool pulley 163. On the other hand, the electric wire 168 is connected to a connector (see 143 in FIG. 2) through the connection portion (see 140 in FIG. 2), and the connector (see 143 in FIG. 2) may be connected to an external power source (not illustrated). Therefore, a predetermined electric energy is transmitted to the jaw 162 through the electric wire 168. Here, the connector (refer to 143 in FIG. 2) may be a monopolar type in which one electrode is formed or a bipolar type in which two electrodes are formed. In the monopolar type, electrical energy of the same polarity may be supplied to two jaws, and in the bipolar type, electrical energy of different polarity may be supplied to the two jaws.

Hereinafter, each component will be described in more detail.

The jaw 162 includes a pinching portion 162a, an extended portion 162b, and a locking portion 162c.

The pinching portion 162a forms the main body of the jaw 162, and a predetermined concave-convex shape may be formed on a surface (inner surface). Although the figure illustrates a dissector as the pinching portion 162a, in addition to this, various types of pinching portion 162a such as forceps and a needle holder may be provided.

The extended portion 162b may be formed to extend from the pinching portion 162a in one direction, for example, in the −X-axis direction, which is the direction in which the connection portion 140 is formed. And, a portion of the extended portion 162b is accommodated in the end tool pulley 163, the jaw 162 and the end tool pulley 163 may be coupled.

The locking portion 162c may be formed to protrude from the extended portion 162b to a certain extent. For example, as illustrated in the drawing, the locking portion 162c may protrude from the extended portion 162b to a certain extent in the Y-axis direction, or the locking portion 162c may protrude from the extended portion 162b to a certain extent in the Z-axis direction. In other words, a portion of the extended portion 162b may be formed to have a step difference from the remaining portion. The locking portion 162c is formed to be caught on a jaw receiving portion 164b of the upper plate 164, which will be described later, so that the jaw 162 may be prevented from being detached from the end tool pulley 163.

The upper plate 164 of the end tool pulley 163 includes a main body 164a, a coupling portion 164b, a jaw receiving portion 164c, a shaft through portion 164d, a wire coupling groove 164e, a wire guide portion 164f and an electric wire guide portion 164g.

The main body 164a is formed in the shape of a substantially circular pulley, and may be formed to be rotatable around a jaw rotation shaft (see 123JA of FIG. 5) coupled to the shaft through portion 164d.

The coupling portion 164b is formed to protrude from the main body 164a toward the jaw 162 to a certain extent. In other words, the coupling portion 164b is formed to extend from the main body 164a in the X-axis direction. In an embodiment of the present disclosure, the coupling portion 164b is formed to protrude from the main body 164a toward the jaw 162 to a certain extent as described above, a distance between the jaw 162 and the wire 166 is increased, and a creepage distance between the jaw 162 and the wire 166 is increased, so that the insulating ability between the jaw 162 and the wire 166 may be strengthened. Here, the creepage distance means the shortest distance between conductors. This will be described in more detail later.

The jaw receiving portion 164c may be formed inside the coupling portion 164b. The jaw receiving portion 164c may be formed in a shape corresponding to the extended portion 162b and the locking portion 162c of the jaw 162 so that the extended portion 162b and the locking portion 162c of the jaw 162 are received or seated in the jaw receiving portion 164c. Here, the jaw receiving portion 164c may be formed to extend to the inside of the main body 164a.

As described above, the locking portion 162c is formed to protrude from the extended portion 162b to a certain extent so that a part of the extended portion 162b is stepped with the remaining portion, and the jaw receiving portion 164c has a shape corresponding to the extended portion 162b and the locking portion 162c of the jaw 162, thus the locking portion 162c is caught on the jaw receiving portion 164b, and it may be prevented that the jaw 162 is detached from the end tool pulley 163. That is, the end tool pulley 163 and jaw 162 may be fixedly coupled by combining the upper plate 164 and the lower plate 165 in a state in which the extended portion 162b and the locking portion 162c of the jaw 162 are accommodated in the jaw receiving portion 164b of the upper plate 164.

The shaft through portion 164d is formed inside the main body 164a, and the jaw rotation shaft (see 123JA in FIG. 5) may be inserted into the shaft through portion 164d. In an embodiment of the present disclosure, the jaw 162 is formed to be spaced apart from the shaft through portion 164d to a certain extent, so that the creepage distance between the jaw 162 and the wire 166 is increased, and the insulating ability between the jaw and the wire may be enhanced. This will be described in more detail later.

The wire coupling groove 164e is formed in a groove shape in the main body 164a, and the fixed coupling portion 167 of the wire 166 is inserted into the wire coupling groove 164e. Therefore, when wire 166 is pulled in one direction, end tool pulley 163 rotates together with wire 166.

The wire guide portion 164f is formed in a groove shape on a side surface of the main body 164a, and serves to guide the path of the wire 166 coupled to the wire coupling groove 164e.

The electric wire guide portion 164g is formed in a groove shape on the side surface of the main body 164a, and serves to guide the path of the electric wire 168 coupled to the jaw 162.

Here, in the end tool pulley assembly 161 of the present disclosure, 1) the end tool pulley 163 includes a ceramic material, 2) the jaw 162 is formed to be spaced apart from the shaft through portion 164d to a certain extent without coupling with the shaft through portion 164d, 3) the coupling portion 164b, which is a neck portion of the end tool pulley 163, is formed to protrude toward the jaw 162 as far as possible to maximize the insulating ability between the jaw 162 and the wire 166. This will be described in more detail as follows.

FIGS. 16 to 20 are views illustrating an end tool pulley assembly used in the prior art. Referring to FIGS. 16 to 20, in the conventional end tool pulley assembly 61, an annular coupling portion 62c is formed at an end of an extended portion of a jaw 62, and the annular coupling portion 62c is fitted to a shaft through portion 64d of an end tool pulley 63, so that the jaw 62 and the end tool pulley 63 are coupled. Such the conventional end tool pulley 63 includes an insulating material such as plastic.

However, in this case, a physical distance between the jaw 62 and a wire 66 (especially a fixed coupling portion) is not long, so when high voltage electrical energy is applied to the jaw 62, an air discharge occurs between the jaw 62 and the wire 66, and the jaw and the wire are electrically connected to each other. That is, the jaw 62 and the wire 66 are energized, resulting in electrical breakdown. And, when the jaw 62 and the wire 66 are energized in this way, heat is generated, which causes damage to each part. In addition, when high-voltage electric energy is applied to a pair of jaws, there is also a problem in that the plastic end tool pulley 63 is burned by flashover occurring between the jaws.

In detail, in the bipolar electric surgical instrument, the maximum voltage is about 500 kV, and sufficient insulation is achieved even with the conventional structure as above. However, in the monopolar electric surgical instrument, the maximum voltage is about 4 kV, and when the structure is formed as above, the jaw 62 and the wire 66 are energized and electrical breakdown occurs. Also, in the monopolar electric surgical instrument, a large voltage is applied between the jaws and a large flashover occurs, and when this flashover touches the end tool pulley 63, the plastic end tool pulley 63 burns or melts.

More specifically, in the end tool pulley of the conventional structure, a distance of the shortest path between the jaw 62 and the wire 66 is a distance from an interface between the jaw 62/end tool pulley 63 to the fixed coupling portion 67 (l1 in FIG. 19), and the creepage distance, which is the shortest distance (l1 in FIG. 19) of this discharge path, is about 1.6 mm. However, when a voltage of about 4 kV is applied in this state, the jaw 62 and the wire 66 are energized, resulting in electrical breakdown.

In addition, if thickness of a neck portion coupled with the jaw 62 in the end tool pulley 63 is formed to be thick in order to solve this problem, a shortest path between the jaw 62 and the wire 66 is between the coupling portion 62c of jaw 62 and the wire 66, the creepage distance which is a shortest distance (l2 in FIG. 20) of this discharge path becomes about 2.43 mm, and when a voltage of 4 kV is applied in this state, the jaw 62 and the wire 66 are energized and electrical breakdown occurs.

In order to solve this problem, In an embodiment of the present disclosure, 1) the end tool pulley 163 includes a ceramic material, 2) the jaw 162 is formed to be spaced apart from the shaft through portion 164d to a certain extent without coupling with the shaft through portion 164d, 3) The thickness of the coupling portion 164b, which is the neck portion of the end tool pulley 163, is formed as thick as possible to maximize the insulating ability between the jaw 162 and the wire 166.

In detail, first, the end tool pulley 163 includes a ceramic material. That is, in the monopolar electric surgical instrument, a strong flashover occurs between the jaws as high voltage is applied. In this case, if the end tool pulley 163 includes a plastic material as in the prior art, the end tool pulley 163 may burn due to flashover. In order to solve this problem, In an embodiment of the present disclosure, the end tool pulley 163 includes a ceramic material with high flame resistance, thereby preventing the end tool pulley 163 from burning.

In addition, the ceramic material itself has a higher dielectric strength than the plastic material that forms the conventional end tool pulley, so a withstand voltage (limit of applied voltage that may be withstand without being destroyed) of the end tool pulley assembly 161 may also be improved.

Figure 18:
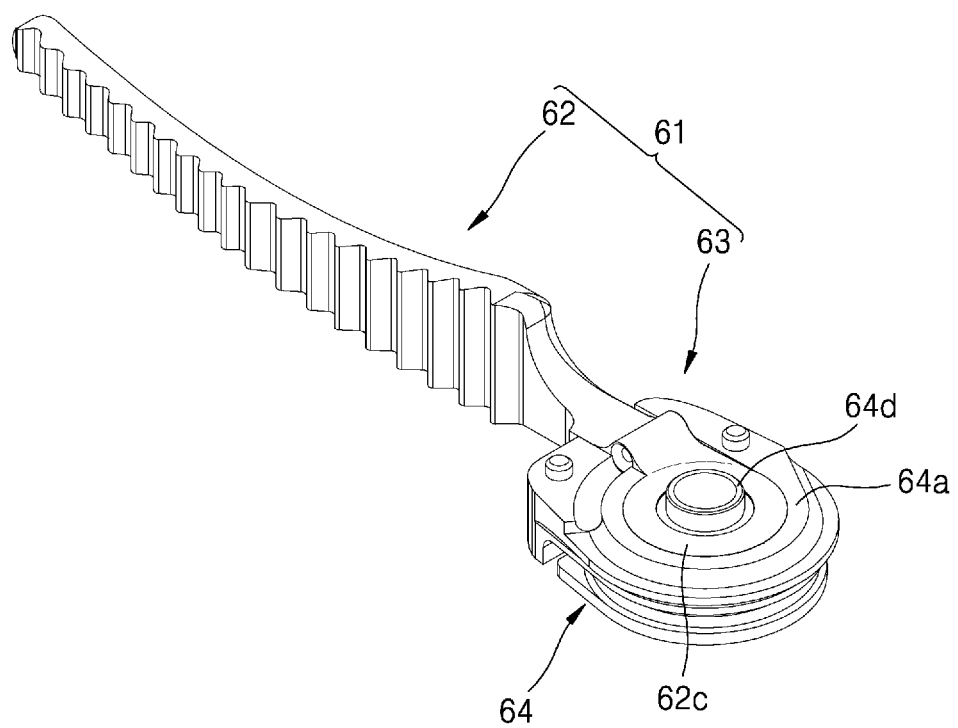
Figure 19:
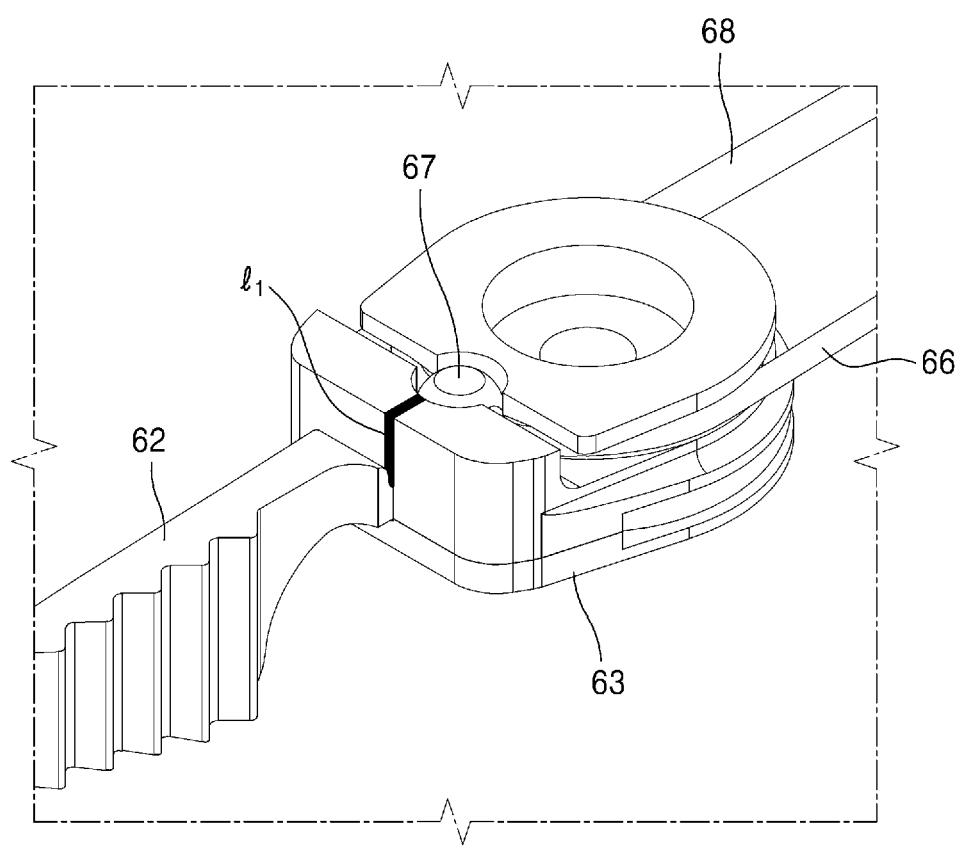
Figure 20:
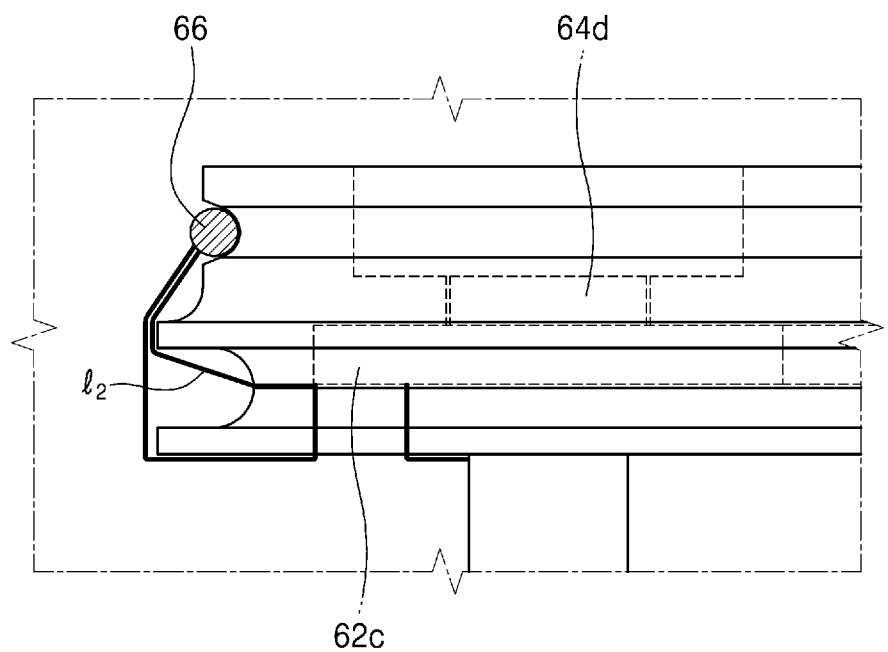

Next, In an embodiment of the present disclosure, the jaw 162 is formed to be spaced apart from the shaft through portion 164d to a certain extent without coupling with the shaft through portion 164d. That is, while there is a physical limit in increasing the distance between the jaw 62 and the wire 66 when the annular coupling portion 62c is formed at the end of the extended portion of the jaw 62 as illustrated in FIG. 18 and the like, the coupling portion 62c is removed, and the jaw 162 is formed to be spaced apart from the shaft through portion 164d to a certain extent, the distance between the jaw 162 and the wire 166 is physically increased, and the creepage distance between the jaw 162 and the wire 166 is increased.

And, in order to couple the jaw 162 and the end tool pulley 163 without such the ring-shaped coupling portion (see 62c of FIG. 18), the extended portion 162b and the locking portion 162c are formed in the jaw 162, and the jaw receiving portion 164c having a shape corresponding to the extended portion 162b and the locking portion 162c is formed in the end tool pulley 163, so that the extended portion 162b and the locking portion 162c are coupled while being accommodated in the jaw receiving portion 164c.

As such, by increasing the creepage distance between the jaw 162 and the wire 166, insulation between the jaw 162 and the wire 166 is secured, and the withstand voltage of the end tool pulley assembly 161 may be improved.

Next, In an embodiment of the present disclosure, in order to maximize the distance from the interface between the jaw 162/end tool pulley 163, which is one of the shortest paths between the jaw 162 and the wire 166, to the fixed coupling portion 167, the coupling portion 164b, which is the neck portion of the end tool pulley 163, is formed to protrude as far as possible from the main body 164a toward the jaw 162 (i.e., in the X-axis direction of the drawing). In this way, the coupling portion 164b is protruded from the main body 164a toward the jaw 162 to a certain extent, so that the distance between the jaw 162 and the wire 166 is increased, thereby increasing the creepage distance between the jaw 162 and the wire 166, and thereby enhancing the insulating ability between the jaw 162 and the wire 166.

According to the present disclosure as described above, in a manually operable surgical instrument for use in laparoscopic surgery or various surgeries, insulating ability between jaws and wires is enhanced, so that the durability of the product may be improved.

Figure 21:
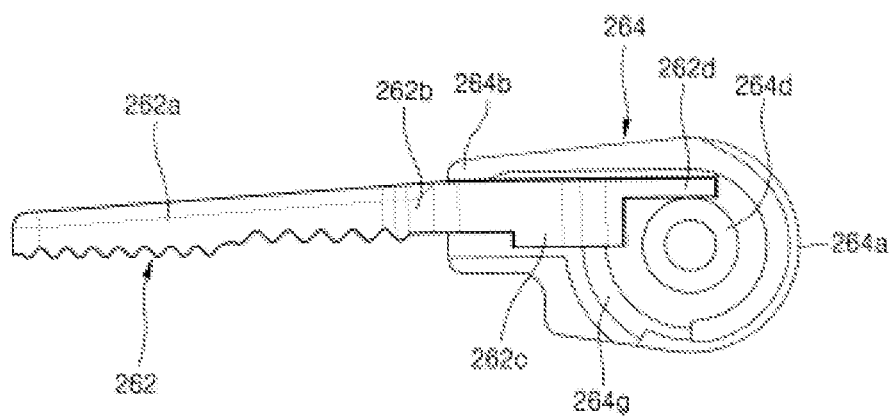
FIG. 21 is a perspective view illustrating an end tool of a surgical instrument according to a second embodiment of the present disclosure.

FIG. 21 is a perspective view illustrating an end tool of a surgical instrument according to a second embodiment of the present disclosure.

Referring to FIG. 21, in the end tool of the surgical instrument according to the second embodiment of the present disclosure, other parts are the same as in the embodiment illustrated in FIG. 2, but it is different from the embodiment of FIG. 2 that a second extended portion 262d is formed to protrude once more in a locking portion 262c of a jaw 262.

In detail, the jaw 262 includes a pinching portion 262a, an extended portion 262b, the locking portion 262c and the second extended portion 262d. And, an upper plate 264 of an end tool pulley 263 includes a main body 264a, a coupling portion 264b, a jaw receiving portion (not illustrated), a shaft through portion 264d, a wire coupling groove (not illustrated), a wire guide portion (not illustrated) and an electric wire guide portion 264g.

Here, the second extended portion 262d may be formed to extend from the locking portion 262c in one direction, for example, in the −X-axis direction, which is the formation direction of the connection portion (see 140 of FIG. 2). In other words, in a state in which the jaw 262 and the end tool pulley 263 are coupled, the second extended portion 262d is formed to protrude from the locking portion 262c toward the shaft through portion 264d to a certain extent. In this case, the second extended portion 262d may be formed to protrude more than a central axis of the shaft through portion 264d in the −X-axis direction.

As such, the second extended portion 262d is formed to protrude more than the central axis of the shaft through portion 264d, so that a contact area between the jaw 262 and the end tool pulley 263 is increased, and the jaw 262 and the end tool pulley 263 may be more stably coupled.

According to the present disclosure as described above, in a manually operable surgical instrument for use in laparoscopic surgery or various surgeries, insulating ability between jaws and wires is enhanced, so that the durability of the product may be improved.

As such, the present disclosure has been described with reference to one embodiment shown in the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

What is claimed is:

1. A surgical instrument for electrocautery, the surgical instrument comprising:
   an end tool comprising:
      at least one jaw formed to enable pitch rotation and yaw rotation thereof; and
      an end tool pulley comprising a shaft through, portion formed to protrude from a main body of the end tool pulley and into which a jaw rotation shaft is inserted therethrough, wherein at least a portion of the at least one jaw is accommodated in the end tool pulley;
   a manipulation portion for controlling rotation of the end tool in two or more directions;
   a power transmission portion comprising a wire connected to the manipulation portion and configured to transfer the rotation of the manipulation portion to the at least one jaw; and
   a connection portion extending in a first direction, and having one end coupled to the end tool and the other end coupled to the manipulation portion, thereby connecting the manipulation portion to the end tool,
   wherein the at least one jaw is not fitted to the jaw rotation shaft and the shaft through portion, does not contact the jaw rotation shaft and the shaft through portion, and is formed to be spaced apart from the jaw rotation shaft and the shaft through portion, and wherein all portions of the at least one jaw are disposed closer to a distal end side of the end tool than all portions of the jaw rotation shaft and the shaft through portion.

2. The surgical instrument of claim 1, wherein the end tool further comprises:

an electric wire connected to the at least one jaw and passing through an inside of the end tool pulley; and an end tool hub axially coupled with the end tool pulley, wherein the end tool pulley accommodating the at least one jaw is rotatable, and wherein the at least one jaw is formed to be spaced apart from the shaft through portion.

3. The surgical instrument of claim 1, wherein the at least one jaw comprises a pinching portion, an extended portion extending in one direction from the pinching portion, and a locking portion protruding from the extended portion, wherein the end tool pulley comprises:

a coupling portion formed in a portion connected to the at least one jaw; and a jaw receiving portion formed in a shape corresponding to the extended portion inside the coupling portion, and wherein at least a portion of the extended portion is received and coupled to the at least one jaw receiving portion.

4. The surgical instrument of claim 3, wherein the locking portion is formed to be caught on the at least one jaw receiving portion of the end tool pulley and the at least one jaw is prevented from being detached from the end tool pulley.

5. The surgical instrument of claim 3, wherein the coupling portion is formed to protrude from a main body of an upper plate of the end tool pulley toward the at least one jaw.

6. The surgical instrument of claim 5, wherein a creepage distance between the wire and the at least one jaw is increased by the coupling portion.

7. The surgical instrument of claim 1, wherein the wire and the at least one jaw are electrically insulated by the end tool pulley.

8. The surgical instrument of claim 1, wherein the end tool pulley comprises an insulator.

9. The surgical instrument of claim 8, wherein the surgical instrument is of a monopolar type.

10. The surgical instrument of claim 8, wherein the end tool pulley comprises ceramic.

11. The surgical instrument of claim 1, wherein the shaft through portion of the end tool pulley and the at least one jaw are not in contact with each other.

* * * * *